(12) United States Patent
Slager

(10) Patent No.: US 12,226,552 B2
(45) Date of Patent: Feb. 18, 2025

(54) ACTIVE AGENT DEPOTS FORMED IN SITU

(71) Applicant: Surmodics, Inc., Eden Prairie, MN (US)

(72) Inventor: Joram Slager, St. Louis Park, MN (US)

(73) Assignee: Surmodics, Inc., Eden Prairie, MN (US)

(*) Notice: Subject to any disclaimer, the term of this patent is extended or adjusted under 35 U.S.C. 154(b) by 106 days.

(21) Appl. No.: 17/038,171

(22) Filed: Sep. 30, 2020

(65) Prior Publication Data

US 2021/0093753 A1 Apr. 1, 2021

Related U.S. Application Data

(60) Provisional application No. 62/908,236, filed on Sep. 30, 2019.

(51) Int. Cl.
| A61L 31/04 | (2006.01) |
|---|---|
| A61L 31/10 | (2006.01) |
| A61L 31/16 | (2006.01) |

(52) U.S. Cl.
CPC ............ *A61L 31/046* (2013.01); *A61L 31/10* (2013.01); *A61L 31/16* (2013.01); *A61L 2300/204* (2013.01); *A61L 2300/252* (2013.01); *A61L 2300/418* (2013.01); *A61L 2300/602* (2013.01); *A61L 2430/36* (2013.01)

(58) Field of Classification Search
CPC ............ A61L 31/046; A61L 2300/204; A61L 2300/418
See application file for complete search history.

(56) References Cited

U.S. PATENT DOCUMENTS

| 3,389,099 A | 6/1968 | Dressler et al. |
|---|---|---|
| 3,936,391 A | 2/1976 | Gabby et al. |
| 4,195,637 A | 4/1980 | Gruntzig et al. |
| 4,456,627 A | 6/1984 | Van Heteren |
| 4,490,421 A | 12/1984 | Levy |
| 4,638,045 A | 1/1987 | Kohn et al. |
| 4,722,906 A | 2/1988 | Guire |
| 4,973,493 A | 11/1990 | Guire |
| 4,973,993 A | 11/1990 | Allen |
| 4,979,959 A | 12/1990 | Guire |
| 5,002,582 A | 3/1991 | Guire et al. |
| 5,041,089 A | 8/1991 | Mueller et al. |
| 5,073,641 A | 12/1991 | Bundgaard et al. |
| 5,087,246 A | 2/1992 | Smith |
| 5,102,402 A | 4/1992 | Dror et al. |
| 5,201,753 A | 4/1993 | Lampropoulos et al. |
| 5,263,992 A | 11/1993 | Guire |
| 5,297,607 A | 3/1994 | Beauchamp |
| 5,304,121 A | 4/1994 | Sahatjian |
| 5,318,587 A | 6/1994 | Davey |
| 5,334,146 A | 8/1994 | Ozasa |
| 5,382,234 A | 1/1995 | Cornelius et al. |
| 5,397,307 A | 3/1995 | Goodin |
| 5,414,075 A | 5/1995 | Swan et al. |
| 5,466,719 A | 11/1995 | Jakobson et al. |
| 5,502,219 A | 3/1996 | Harris |
| 5,512,329 A | 4/1996 | Guire et al. |
| 5,556,383 A | 9/1996 | Wang et al. |
| 5,558,642 A | 9/1996 | Schweich, Jr. et al. |
| 5,571,089 A | 11/1996 | Crocker |
| 5,585,506 A | 12/1996 | Harvey |
| 5,616,608 A | 4/1997 | Kinsella et al. |
| 5,632,773 A | 5/1997 | Graham et al. |
| 5,637,460 A | 6/1997 | Swan et al. |
| 5,714,360 A | 2/1998 | Swan et al. |
| 5,728,732 A | 3/1998 | Corey |
| 5,741,551 A | 4/1998 | Guire et al. |
| 5,776,101 A | 7/1998 | Goy |
| 5,807,331 A | 9/1998 | Den Heijer et al. |

(Continued)

FOREIGN PATENT DOCUMENTS

| CA | 2836266 | 11/2012 |
|---|---|---|
| CA | 2890205 | 5/2014 |

(Continued)

OTHER PUBLICATIONS

Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative," Pharmaceutical Research, vol. 12, No. 3, 1995 1995, 397-405.

Avella, "Addition of glycerol plasticizer to seaweeds derived alginates: Influences of microstructure on chemical-physical properties," Carbohydrate Polymers vol. 69, Issue 3, Jun. 25, 2007, 503-511.

Babayan, V K. "Preparation and Properties of Some Polyglycerol Esters of Short and Medium Length Fatty Acids," Journal of the American Oil Chemists' Society Jul. 1971 Jul. 1971, 307-309.

Babayan, V K et al., "Nutritional Studies of Polyglycerol Esters," The Journal of the American Oil Chemist' Society vol. 41, Jun. 1964 Jun. 1964, 434-438.

(Continued)

*Primary Examiner* — Robert A Wax
*Assistant Examiner* — William Craigo
(74) *Attorney, Agent, or Firm* — Pauly, DeVries Smith & Deffner LLC

(57) ABSTRACT

Embodiments herein relate to active agent depots formed in situ and related methods. In various embodiments, a method of forming an active agent depot in situ is included. The method can include contacting a composition with a vessel wall, wherein the composition includes an active agent and a fibrin promoting vessel wall transfer agent wherein the ratio of active agent to fibrin promoting vessel wall transfer agent (wt./wt.) is at least 5:1. The method also includes transferring the composition from a device surface to the vessel wall surface. The method also includes forming a fibrin matrix around the composition. Other embodiments are also included herein.

15 Claims, 10 Drawing Sheets

(56) References Cited

U.S. PATENT DOCUMENTS

| | | |
|---|---|---|
| 5,811,447 A | 9/1998 | Kunz et al. |
| 5,833,657 A | 11/1998 | Reinhardt et al. |
| 5,858,653 A | 1/1999 | Duran et al. |
| 5,882,336 A | 3/1999 | Janacek |
| 5,891,451 A | 4/1999 | Guerrero et al. |
| 5,980,948 A | 11/1999 | Goedemoed et al. |
| 6,007,833 A | 12/1999 | Chudzik et al. |
| 6,077,698 A | 6/2000 | Swan et al. |
| 6,168,748 B1 | 1/2001 | Wang et al. |
| 6,177,522 B1 | 1/2001 | Brady et al. |
| 6,210,364 B1 | 4/2001 | Anderson et al. |
| 6,278,018 B1 | 8/2001 | Swan |
| 6,299,604 B1 | 10/2001 | Ragheb et al. |
| 6,328,710 B1 | 12/2001 | Wang et al. |
| 6,340,465 B1 | 1/2002 | Hsu et al. |
| 6,394,995 B1 | 5/2002 | Solar et al. |
| 6,436,440 B1 | 8/2002 | Meffert et al. |
| 6,444,324 B1 | 9/2002 | Sjoquist et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,506,895 B2 | 1/2003 | Guire et al. |
| 6,514,734 B1 | 2/2003 | Clapper et al. |
| 6,515,009 B1 | 2/2003 | Kunz et al. |
| 6,517,515 B1 | 2/2003 | Eidenschink |
| 6,544,544 B2 | 4/2003 | Hunter et al. |
| 6,603,040 B1 | 8/2003 | Swan |
| 6,613,066 B1 | 9/2003 | Fukaya et al. |
| 6,620,904 B2 | 9/2003 | Lemke |
| 6,623,452 B2 | 9/2003 | Chien et al. |
| 6,623,504 B2 | 9/2003 | Vrba et al. |
| 6,663,662 B2 | 12/2003 | Pacetti et al. |
| 6,703,040 B2 | 3/2004 | Katsarava et al. |
| 6,730,064 B2 | 5/2004 | Ragheb et al. |
| 6,762,019 B2 | 7/2004 | Swan et al. |
| 6,896,842 B1 | 5/2005 | Hamilton et al. |
| 7,034,765 B2 | 4/2006 | Fischer et al. |
| 7,138,541 B2 | 11/2006 | Swan |
| 7,163,523 B2 | 1/2007 | Devens, Jr. et al. |
| 7,309,593 B2 | 12/2007 | Ofstead et al. |
| 7,348,055 B2 | 3/2008 | Chappa et al. |
| 7,438,710 B2 | 10/2008 | Anderson et al. |
| 7,507,469 B2 | 3/2009 | Yao et al. |
| 7,696,259 B2 | 4/2010 | Hanley et al. |
| 7,731,685 B2 | 6/2010 | Schaeffer et al. |
| 7,736,689 B2 | 6/2010 | Chappa et al. |
| 7,758,892 B1 | 7/2010 | Chen et al. |
| 7,772,393 B2 | 8/2010 | Guire et al. |
| 7,797,033 B2 | 9/2010 | D'Andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,034,765 B2 | 10/2011 | De et al. |
| 8,039,524 B2 | 10/2011 | Ralph et al. |
| 8,158,106 B2 | 4/2012 | Guire et al. |
| 8,172,793 B2 | 5/2012 | Choules et al. |
| 8,202,530 B2 | 6/2012 | Hossainy et al. |
| 8,246,576 B2 | 8/2012 | Slager |
| 8,257,305 B2 | 9/2012 | Scheller et al. |
| 8,293,262 B2 | 10/2012 | Chen et al. |
| 8,439,868 B2 | 5/2013 | Scheller et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao et al. |
| 8,663,674 B2 | 3/2014 | Wen et al. |
| 8,673,387 B2 | 3/2014 | Bates et al. |
| 8,697,112 B2 | 4/2014 | Ditizio et al. |
| 8,809,411 B2 | 8/2014 | Rooijmans |
| 8,871,819 B2 | 10/2014 | Meyering et al. |
| 8,889,760 B2 | 11/2014 | Kurdyumov et al. |
| 8,952,103 B2 | 2/2015 | Blondel et al. |
| 9,375,517 B2 | 6/2016 | Babcock |
| 9,555,119 B2 | 1/2017 | Ventura et al. |
| 9,757,497 B2 | 9/2017 | Slager |
| 9,782,516 B2 | 10/2017 | Pacetti et al. |
| 9,861,727 B2 | 1/2018 | Slager et al. |
| 9,999,675 B2 | 6/2018 | Ventura et al. |
| 10,058,634 B2 | 8/2018 | Chappa et al. |
| 10,213,528 B2 | 2/2019 | Slager et al. |
| 10,213,529 B2 | 2/2019 | Slager |
| 10,617,793 B2 | 4/2020 | Slager et al. |
| 10,898,446 B2 | 1/2021 | Kloke |
| 2002/0006493 A1 | 1/2002 | Chabrecek et al. |
| 2002/0082680 A1* | 6/2002 | Shanley .................. A61F 2/91 623/1.42 |
| 2002/0123801 A1 | 9/2002 | Pacetti et al. |
| 2003/0065355 A1 | 4/2003 | Weber |
| 2003/0195611 A1 | 10/2003 | Greenhalgh et al. |
| 2003/0211135 A1 | 11/2003 | Greenhalgh et al. |
| 2004/0044404 A1 | 3/2004 | Stucke et al. |
| 2004/0051201 A1 | 3/2004 | Greenhalgh et al. |
| 2004/0105839 A1 | 6/2004 | Park |
| 2004/0117007 A1 | 6/2004 | Whitbourne et al. |
| 2005/0100580 A1 | 5/2005 | Osborne et al. |
| 2005/0187605 A1 | 8/2005 | Greenhalgh et al. |
| 2005/0255142 A1 | 11/2005 | Chudzik et al. |
| 2005/0281857 A1 | 12/2005 | Heyer et al. |
| 2006/0018948 A1 | 1/2006 | Guire et al. |
| 2006/0020243 A1 | 1/2006 | Speck et al. |
| 2006/0030669 A1 | 2/2006 | Taton et al. |
| 2006/0148982 A1 | 7/2006 | Uchegbu et al. |
| 2006/0200232 A1 | 9/2006 | Phaneuf et al. |
| 2006/0240194 A1 | 10/2006 | Lemke et al. |
| 2007/0026037 A1 | 2/2007 | Kloke et al. |
| 2007/0032882 A1 | 2/2007 | Lodhi et al. |
| 2007/0048351 A1 | 3/2007 | Lunn |
| 2007/0065481 A1 | 3/2007 | Chudzik et al. |
| 2007/0128343 A1* | 6/2007 | Chappa .................. B05B 17/06 118/300 |
| 2007/0154591 A1 | 7/2007 | Andersen |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0020013 A1 | 1/2008 | Reyes et al. |
| 2008/0220054 A1 | 9/2008 | Shastri et al. |
| 2008/0233183 A1 | 9/2008 | McCook et al. |
| 2009/0030504 A1 | 1/2009 | Weber et al. |
| 2009/0043276 A1 | 2/2009 | Weber et al. |
| 2009/0043378 A1 | 2/2009 | Cheng et al. |
| 2009/0081276 A1 | 3/2009 | Alsberg et al. |
| 2009/0221767 A1 | 9/2009 | Malet |
| 2009/0226501 A1 | 9/2009 | Parsonage et al. |
| 2009/0227946 A1 | 9/2009 | Kangas |
| 2010/0015240 A1 | 1/2010 | Biggs |
| 2010/0040766 A1 | 2/2010 | Chappa et al. |
| 2010/0076377 A1 | 3/2010 | Ehrenreich et al. |
| 2010/0076401 A1 | 3/2010 | Von et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0198168 A1 | 8/2010 | Rooijmans |
| 2010/0272774 A1 | 10/2010 | Chappa |
| 2010/0274012 A1 | 10/2010 | Guire et al. |
| 2010/0292668 A1 | 11/2010 | Slager |
| 2011/0008260 A1 | 1/2011 | Flanagan et al. |
| 2011/0022027 A1 | 1/2011 | Morishita et al. |
| 2011/0046255 A1 | 2/2011 | Rooijmans |
| 2011/0059874 A1 | 3/2011 | Rooijmans et al. |
| 2011/0092919 A1* | 4/2011 | Pierce .................. A61M 5/315 435/325 |
| 2011/0144373 A1 | 6/2011 | Swan et al. |
| 2011/0245367 A1 | 10/2011 | Kurdyumov et al. |
| 2011/0250255 A1 | 10/2011 | Parsonage et al. |
| 2011/0257339 A1 | 10/2011 | Fischer et al. |
| 2011/0275725 A1 | 11/2011 | Meyering et al. |
| 2012/0039983 A1 | 2/2012 | Uhrich et al. |
| 2012/0046384 A2 | 2/2012 | Kurdyumov et al. |
| 2012/0083734 A1 | 4/2012 | Ayres et al. |
| 2012/0148852 A1 | 6/2012 | Jelle et al. |
| 2012/0149934 A1 | 6/2012 | Kurdyumov |
| 2012/0177742 A1 | 7/2012 | McClain et al. |

(56) References Cited

U.S. PATENT DOCUMENTS

| | | |
|---|---|---|
| 2012/0177910 A1 | 7/2012 | Weber et al. |
| 2012/0296274 A1 | 11/2012 | Slager |
| 2013/0143056 A1 | 6/2013 | Swan et al. |
| 2013/0190689 A1 | 7/2013 | Slager |
| 2013/0197433 A1 | 8/2013 | Babcock |
| 2013/0302529 A1 | 11/2013 | Kurdyumov |
| 2014/0004158 A1 | 1/2014 | McGonigle |
| 2014/0142166 A1 | 5/2014 | Ventura |
| 2014/0162083 A1 | 6/2014 | Kurdyumov et al. |
| 2014/0193474 A1 | 7/2014 | Babcock et al. |
| 2014/0276636 A1 | 9/2014 | Lee et al. |
| 2014/0277399 A1* | 9/2014 | Pacetti ............... A61L 27/3604 623/1.42 |
| 2014/0336571 A1 | 11/2014 | Slager |
| 2015/0140107 A1* | 5/2015 | Slager ................ C12N 15/113 514/44 A |
| 2015/0283092 A1 | 10/2015 | Ruddy et al. |
| 2017/0072057 A1 | 3/2017 | Ventura et al. |
| 2017/0112973 A1 | 4/2017 | Slager et al. |
| 2018/0110903 A1 | 4/2018 | Slager et al. |
| 2018/0169032 A1 | 6/2018 | Kloke |
| 2018/0272040 A1 | 9/2018 | Chappa et al. |
| 2019/0290804 A1* | 9/2019 | Askari ................. A61K 9/0024 |
| 2020/0237971 A1 | 7/2020 | Slager et al. |

FOREIGN PATENT DOCUMENTS

| | | |
|---|---|---|
| CN | 1413118 | 4/2003 |
| CN | 1950114 | 4/2007 |
| CN | 1964750 | 5/2007 |
| CN | 102036696 | 4/2011 |
| EP | 0882461 | 12/1998 |
| EP | 1176993 | 6/2003 |
| EP | 1430917 | 6/2004 |
| EP | 1994950 | 11/2008 |
| EP | 1997525 | 12/2008 |
| EP | 2019695 | 2/2009 |
| EP | 2251050 | 11/2010 |
| EP | 2098230 | 6/2012 |
| EP | 2292225 | 6/2012 |
| JP | 10328293 | 12/1998 |
| JP | H11322586 | 11/1999 |
| JP | 2003506417 | 2/2003 |
| JP | 2006500437 | 1/2006 |
| JP | 2006508912 | 3/2006 |
| JP | 2007537005 | 12/2007 |
| JP | 2008519771 | 6/2008 |
| JP | 2009502243 | 1/2009 |
| WO | 9964086 | 12/1999 |
| WO | 0110468 | 2/2001 |
| WO | 2001045742 | 6/2001 |
| WO | 03055611 | 7/2003 |
| WO | 2004017943 | 5/2004 |
| WO | 2005079754 | 9/2005 |
| WO | 2005113034 | 12/2005 |
| WO | 2006019848 | 2/2006 |
| WO | 2006026187 | 3/2006 |
| WO | 2006053175 | 5/2006 |
| WO | 2007012051 | 1/2007 |
| WO | 2007106441 | 9/2007 |
| WO | 2007136504 | 11/2007 |
| WO | 2009051614 | 4/2009 |
| WO | 2009113605 | 9/2009 |
| WO | 2009121629 | 10/2009 |
| WO | 2010111517 | 9/2010 |
| WO | 2010129328 | 11/2010 |
| WO | 2011005421 | 1/2011 |
| WO | 2011024831 | 3/2011 |
| WO | 2011052089 | 5/2011 |
| WO | 2011143237 | 11/2011 |
| WO | 2012003293 | 1/2012 |
| WO | 2012162061 | 11/2012 |
| WO | 2013109930 | 7/2013 |
| WO | 2013169879 | 11/2013 |
| WO | 2014071387 | 5/2014 |
| WO | 2014186729 | 11/2014 |
| WO | 2016123480 | 8/2016 |
| WO | 2018118671 | 6/2018 |

OTHER PUBLICATIONS

Birnbaum, Duane T. et al., "Microparticle Drug Delivery Systems," Chapter 6, Drug Delivery Systems in Cancer Therapy, 2003, (pp. 117-135).
Bodansky, M et al., "Utilization of Polyglycerol Esters," Biochemistry vol. 32 Aug. 30, 1938, 1938-1942.
Brunot, Celine et al., "Cytoxicity of Polyethyleneimine (PEI), Precursor Base Layer of Polyelectrolyte Multilayer Films," Biomaterials, 2007. 28(4): p. 632-40 (9 pages).
Byrne, Robert A. "Drug-Coated Balloon Therapy in Coronary and Peripheral Artery Disease," Nat Rev Cardiol, 2014. 11(1): p. 13-23 (11 pages).
Chaabane, Chiraz "Biological Responses in Stented Arteries," Cardiovasc Res, 2013. 99(2): p. 353-63 (11 pages).
Charlemagne, D et al., "Enzymatic Synthesis of Polyglycerol-Fatty Acid Esters in a Solvent-Free System," Journal for American Oil Chemists' Society vol. 72. No. 1 (1995) 1995, 61-65.
"Communication Pursuant to Article 94(3) EPC," For European Application No. 10716714, mailed on Feb. 13, 2015 (6 pages).
"Communication Pursuant to Article 94(3) EPC," for European Application No. 10716714, mailed on Jan. 18, 2013 (5 pages).
"Communication Pursuant to Article 94(3) EPC," for European Application No. 13792207.6, mailed Sep. 29, 2017 (5 pages).
"Communication Pursuant to Article 94(3) EPC," for European Patent Application No. 12723063.9 mailed Jan. 16, 2019 (5 pages).
"Communication Pursuant to Article 94(3) EPC," for European Patent Application No. 12723063.9 mailed Jun. 12, 2017 (5 pages).
"Communication Pursuant to Article 94(3) EPC," for European Patent Application No. 14730381.2 mailed Nov. 21, 2017 (4 pages).
"Communication Pursuant to Article 94(3) EPC," for European Patent Application No. 16703247.3 mailed Apr. 23, 2019 (5 pages).
"Communication Pursuant to Article 94(3) EPC," for European Patent Application No. 16703247.3 mailed Feb. 12, 2020 (7 pages).
"Communication Pursuant to Article 94(3) EPC," for European Patent Application No. 16703247.3 mailed Sep. 4, 2018 (5 pages).
"Communication Pursuant to Article 94(3) EPC," for European Patent Application No. 17835893.3 mailed Jun. 29, 2020 (5 pages).
De Meulenaer, B et al., "Development of Chromatographic Method for the Determination of Degree of Polymerisation of Polyglycerols and Polyglycerol Fatty Acid Esters," Chromatographia vol. 51, No. 1/2, Jan. 2000 Jan. 2000, 44-52.
"Decision of Refusal," for Japanese Patent Application No. 2012-508637, mailed Feb. 3, 2015 (3 pages) with English summary.
"Decision of Rejection," for Chinese Patent Application No. 201510411761.0 mailed Nov. 30, 2018 (19 pages) with English Translation.
Dobson, Kevin S. et al., "The Preparation of Polyglycerol Esters Suitable as Low-Caloric Fat Substitutes," Journal of The American Oil Chemists' Society vol. 70, No. 11 (Nov. 1993) Nov. 1993, 1089-1092.
Dow Corning Corp., "A guide to Silane Solutions," 2005 (30 pages).
FAO Nutrition Meetings Report, "Toxicological Evaluation Of Some Antimicrobials, Antioxidants, Emulsifiers, Stabilizers, Flour-treatment Agents, Acids And Bases," FAO Nutrition Meetings Report Series No. 40a, B, C Who/ Food Add. 67.29 1966, 1-4.
"File History," for U.S. Appl. No. 12/769,127, retrieved Apr. 7, 2021 (487 pages).
"File History," for U.S. Appl. No. 13/469,844, retrieved Apr. 7, 2021 (395 pages).
"File History," for U.S. Appl. No. 13/793,390 retrieved Apr. 7, 2021 (371 pages).
"File History," for U.S. Appl. No. 14/072,520, retrieved Apr. 7, 2021 (192 pages).
"File History," for U.S. Appl. No. 14/280,170 retrieved Apr. 12, 2021 (669 pages).
"File History," for U.S. Appl. No. 14/609,270, retrieved Apr. 12, 2021 (343 pages).

(56) References Cited

OTHER PUBLICATIONS

"File History," for U.S. Appl. No. 15/357,496 retrieved Apr. 12, 2021 (149 pages).
"File History," for U.S. Appl. No. 15/385,112, retrieved Apr. 19, 2021 (252 pages).
"File History," for U.S. Appl. No. 15/840,540, retrieved Apr. 19, 2021 (304 pages).
"File History," for U.S. Appl. No. 15/850,010 retrieved Apr. 19, 2021 (223 pages).
"File History," for U.S. Appl. No. 15/994,263 retrieved Apr. 19, 2021 (199 pages).
"Final Rejection," from CN Application No. 201080018767.7, mailed Jan. 6, 2014 (10 pages).
Finkel, Toren "Relief with Rapamycin: mTOR Inhibition Protects Against Radiation-Induced Mucositis," Cell Stem Cell, vol. 11:3, Sep. 7, 2012 (pp. 1-4).
"First Examination Report," for Indian Patent Application No. 201747029823 mailed Nov. 25, 2019 (6 pages).
"First Examination Report," for Indian Patent Application No. 3723/KOLNP/2013 mailed Sep. 28, 2018 (5 pages).
"First Office Action," for Chinese Application No. 201080018767.7 mailed Jun. 8, 2013 (9 pages).
"First Office Action," for Chinese Patent Application No. 2012800328049, mailed Mar. 2, 2015 (12 pages) including English translation.
"First Office Action," for Chinese Patent Application No. 201510411761.0 mailed Jun. 30, 2017 (13 pages) with English translation.
"First Office Action," for Chinese Patent Application No. 2016800187265 mailed Nov. 5, 2019 (9 pages) with English Translation.
"First Office Action," for Russian Patent Application No. 2017129933 mailed Jun. 27, 2019 (10 pages) with English Translation.
"Fourth Office Action," for Chinese Patent Application No. 2012800328049, mailed May 3, 2017 (8 pages) with English translation.
From Wikipedia, "Electrospinning," From Wikipedia, the free encyclopedia, http://en.wikipedia.org/wiki/Electrospinning, downloaded Sep. 13, 2010; last updated Sep. 2, 2010, 2009, (pp. 1-6).
Ghonaim, Hassan M. et al., "N1, N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29) Oct. 30, 2009.
Hagemeier, C J. "Ocular Tolerability of Poly(lactide-co-glyoliide) Microspheres Following Subconjunctival and Intravitreal Injection in Rabbit Eyes," ARVO 2010 Presented ARVO 2010, Hall B/C, May 6, 2010 8:30am-10:15am May 6, 2010.
Howes, D et al., "The Fate of Ingested Glyceran Esters of Condensed Castor Oil Fatty Acids [Polyglycerol Polyricinoleate (PGPR)] in the Rat," Food and Chemical Toxicology 36 (1998) 719-738 1998, 719-738.
"International Preliminary Report on Patentability," for PCT Application No. PCT/US2016/015644 mailed Aug. 10, 2017 (12 pages).
"International Preliminary Report on Patentability," for PCT Application No. PCT/US2017/066573 mailed Jul. 4, 2019 (7 pages).
"International Preliminary Report on Patentability," for PCT/US2012/038158, mailed Nov. 28, 2013 (8 pages).
"International Preliminary Report on Patentability," for PCT/US2013/068539, mailed May 14, 2015 (9 pages).
"International Preliminary Report on Patentability," for PCT/US2014/038435 mailed Nov. 26, 2015 (10 pages).
"International Search Report & Written Opinion," for PCT/US2016/015644 mailed Jul. 11, 2016 (17 pages).
"International Search Report and Written Opinion," for PCT Application No. PCT/US2017/066573 mailed Apr. 3, 2018 (10 pages).
"International Search Report and Written Opinion," for PCT/US2010/032741 mailed Dec. 13, 2010 (11 pages). Dec. 13, 2010, 11 pages.
"International Search Report and Written Opinion," for PCT/US2012/038158, mailed Sep. 27, 2012 (13 pages).
"International Search Report and Written Opinion," for PCT/US2013/068539, mailed Jan. 22, 2014 (12 pages).
"International Search Report and Written Opinion," for PCT/US2014/038435, mailed Aug. 25, 2014 (13 pages).
"Invitation to Pay Additional Fees and Partial Search Report," for PCT Application No. PCT/US2016/015644, mailed May 3, 2016 (8 pages).
"Invitation to Respond to Written Opinion," for SG Patent Application No. 201107896-1, mailed Jun. 12, 2012 (6 pages).
Kallinteri, Paraskevi et al., "Novel Functionalized Biodegradable Polymers for Nanoparticle Drug Delivery Systems," Biomacromolecules 2005 2006, 6, 1885-1894; American Chemical Society Apr. 27, 2005, 1885-1894.
Kumar, Majeti N.V. R. "Nano and Microparticles as Controlled Drug Delivery Devices," J. Pharm Pharmaceut Sci, 3(2), 2000 (pp. 234-258).
Liu, Rong "Water-Insoluble Drug Formulation," CRC Press, 2nd Ed., 2008 (pp. 1-3).
Love, Kevin T. et al., "Lipid-Like Materials for Low-Dose In Vivo Gene Silencing," PNAS Feb. 2010, 107 (5) 1864-1869, www.pnas.org/cgi/doi/10.1073/pnas.0910603106 (6 pages).
McIntyre, R T. "Polyglycerol esters," Journal of American Oil Chemists' Society Nov. 1979 (vol. 56) Nov. 1979, 835A-840A.
Mugabe, Clement et al., "Paclitaxel Incorporated in Hydrophobically Derivatized Hyperbranched Polyglycerols for Intravesical Bladder Cancer Therapy," BJU International, 2008, vol. 103, p. 978-986.
"Non-Final Office Action," for Japanese Patent Application No. 2012-508637, mailed Mar. 18, 2014 (4 pages) with English translation.
"Non-Final Office Action," for Mexican Patent Application No. MX/a/2011/011389, mailed Aug. 18, 2015 (1 page).
"Non-Final Office Action," for Mexican Patent Application No. MX/a/2011/011389, mailed Feb. 22, 2016 (1 page).
"Non-Final Office Action," for U.S. Appl. No. 16/847,272 mailed Jan. 7, 2021 (36 pages).
"Notification for Patent Reexamination," for Chinese Patent Application No. 201080018767.7, mailed Sep. 25, 2014 (12 pages) with English translation.
"Office Action Response," for Israeli Patent Application No. 242545 filed Sep. 28, 2019 (133 pages) English Translation.
"Office Action," for Canadian Patent Application No. 2,760,187 mailed Jan. 12, 2017 (3 pages).
"Office Action," for Canadian Patent Application No. 2,760,187 mailed Mar. 24, 2016 (4 pages).
"Office Action," for Canadian Patent Application No. 2,836,266 mailed Apr. 11, 2018 (3 pages).
"Office Action," for Canadian Patent Application No. 2,836,266 mailed Jul. 23, 2020 (3 pages).
"Office Action," for Canadian Patent Application No. 2,836,266 mailed Nov. 30, 2018 (4 pages).
"Office Action," for Canadian Patent Application No. 2,836,266 mailed Oct. 23, 2019 (3 pages).
"Office Action," for Canadian Patent Application No. 2,890,205 mailed Sep. 18, 2019 (5 pages).
"Office Action," for Canadian Patent Application No. 2,912,690 mailed Apr. 29, 2020 (5 pages).
"Office Action," for Canadian Patent Application No. 2,912,690 mailed Feb. 23, 2021 (3 pages).
"Office Action," for Canadian Patent Application No. 2,912,690 mailed Nov. 5, 2020 (3 pages).
"Office Action," for Israeli Patent Application No. 242545 mailed Feb. 6, 2020 (7 pages) with English Translation.
"Office Action," for Israeli Patent Application No. 242545 mailed May 28, 2019 (8 pages) with English Translation.
"Office Action," for Israeli Patent Application No. 253612 mailed Jul. 31, 2020 (8 pages) with English Translation.
"Office Action," for Japanese Patent Application No. 2014511494 mailed Feb. 5, 2016 (13 pages) with English Translation.
"Office Action," for Japanese Patent Application No. 2014511494 mailed Nov. 25, 2016 (6 pages) with English Translation.
"Office Action," for Japanese Patent Application No. 2015-540868 mailed Aug. 31, 2017 (10 pages) with English translation.

(56) References Cited

OTHER PUBLICATIONS

"Office Action," for Japanese Patent Application No. 2015-540868 mailed May 21, 2018 (6 pages) with English translation.
"Office Action," for Japanese Patent Application No. 2016-514136 mailed Apr. 10, 2018 (7 pages) with English translation.
"Office Action," for Japanese Patent Application No. 2017-540169 mailed Jul. 30, 2020 (9 pages) with English Translation.
"Office Action," for Japanese Patent Application No. 2017-540169 mailed Nov. 21, 2019 (12 pages) with English Translation.
"Office Action," for Mexican Patent Application No. MX/a/2015/015589 mailed Sep. 9, 2018 (1 page), translation only.
"Office Action," for Mexican Patent Application No. MX/a/2017/009688 mailed Dec. 10, 2020 (6 pages) with English Translation.
"Office Action," for Mexican Patent Application No. MX/a/2017/009688 mailed Jul. 14, 2020 (5 pages) with English Translation.
"Office Action," for Russian Patent Application No. 2017129933 mailed Mar. 2, 2020 (9 pages) with English Translation.
"Office Action," for Russian Patent Application No. 2017129933 mailed Oct. 21, 2019 (9 pages) with English Translation.
Ong, B.C. et al., "Interparticle Forces in Spherical Monodispersed Silica Dispersions: Effects of Branched Polyethylenimine and Molecular Weight," Journal of Colloid and Interface Science, 2009. 337(1): p. 24-31 (8 pages).
Orafei, Hossein et al., "Novel Poly(glycerol-adipate) Polymers Used for Nanoparticle Making: A Study of Surface Free Energy," Iranian Journal of Pharmaceutical Research (2008), 7 (1): 11-19 2008, 11-19.
"PCT Notification Concerning Transmittal of Copy of International Preliminary Report on Patentability," from International Application No. PCT/US10/032741, mailed Nov. 10, 2011, pp. 1-8, 8.
"Preliminary Office Action," for Brazilian Patent Application No. 1120170136420 mailed Oct. 15, 2019 (7 pages) with English Translation.
"Product Data Sheet," for PEBAX MV 1074 SA 01 MED from Arkema (2013, pp. 1-2) 2 pages.
Puri, Sanyogita "Drug Incorporation and Release of Water Soluble Drugs from Novel Functionalized Poly(glycerol adipate) Nanoparticles," Journal of Controlled Release 125 (2008) Oct. 10, 2007, 59-67.
"Reexamination Notification," for Chinese Patent Application No. 201510411761.0 mailed Jun. 3, 2020 (13 pages) with English Translation.
Renkin, Eugene M. "Filtration, Diffusion, and Molecular Sieving Through Porous Cellulose Membranes," Nov. 20, 1954 (pp. 1-19).
"Response to Communication Pursuant to Article 94(3) EPC," for European Application No. 10716714.0 filed with EPO Aug. 11, 2015 (51 pages).
"Response to Communication Pursuant to Article 94(3) EPC," for European Application No. 10716714.0 filed with EPO Jun. 10, 2013 (9 pages).
"Response to communication Pursuant to Article 94(3) EPC," for European Patent Application No. 12723063.9 filed Jul. 2, 2019 (56 pages).
"Response to Communication Pursuant to Article 94(3) EPC," for European Patent Application No. 12723063.9 filed with the EPO Nov. 16, 2017 (9 pages).
"Response to Communication Pursuant to Article 94(3) EPC," for European Patent Application No. 13792207.6, filed with the EPO Mar. 29, 2018 (25 pages).
"Response to Communication Pursuant to Article 94(3) EPC, " for European Patent Application No. 14730381.2, filed with the European Patent Office Dec. 21, 2017 (68 pages).
"Response to Communication Pursuant to Article 94(3) EPC," for European Patent Application No. 16703247.3 filed Aug. 11, 2020 (10 pages).
"Response to Communication Pursuant to Article 94(3) EPC," for European Patent Application No. 16703247.3 filed Aug. 30, 2019 (10 pages).
"Response to Communication Pursuant to Article 94(3) EPC," for European Patent Application No. 16703247.3 filed Dec. 20, 2018 (7 pages).
"Response to Communication Pursuant to Article 94(3) EPC," for European Patent Application No. 17835893.3 filed Oct. 29, 2020 (7 pages).
"Response to Communication Pursuant to Rule 161 and 162 EPC," for European Patent Application 12723063.9, mailed Jan. 21, 2014 and filed with the EPO Jul. 18, 2014 (4 pages).
"Response to Communication Pursuant to Rules 161(1) and 162 EPC," for European Application No. 13792207.6, filed with the EPO Feb. 3, 2016 (4 pages).
"Response to Communication Pursuant to Rules 161(1) and 162 EPC," for European Patent Application No. 14730381.2, filed with the European Patent Office Jul. 14, 2016 (14 pages).
"Response to Communication Pursuant to Rules 161(1) and 162 EPC," for European Patent Application No. 17835893.3 filed Jan. 21, 2020 (7 pages).
"Response to Communication Pursuant to Rules 161(1) and 162 EPC," for European Patent No. 16703247.3 filed with the EPO on Mar. 22, 2018.
"Response to First Examination Report," for Indian Patent Application No. 201747029823 filed May 22, 2020 (13 pages).
"Response to First Examination Report," for Indian Patent Application No. 3723/KOLNP/2013 filed Feb. 20, 2019 (23 pages).
"Response to Office Action," for Canadian Patent Application No. 2,760,187 filed with CIPO Feb. 15, 2017 (5 pages).
"Response to Office Action," for Canadian Patent Application No. 2,760,187 filed with CIPO Sep. 22, 2016 (22 pages).
"Response to Office Action," for Canadian Patent Application No. 2,836,266 filed Apr. 15, 2020 (18 pages).
"Response to Office Action," for Canadian Patent Application No. 2,836,266 filed May 29, 2019 (19 pages).
"Response to Office Action," for Canadian Patent Application No. 2,836,266 filed Oct. 19, 2020 (8 pages).
"Response to Office Action," for Canadian Patent Application No. 2,836,266 filed with CIPO Sep. 20, 2018 (28 pages).
"Response to Office Action," for Canadian Patent Application No. 2,890,205 filed Mar. 18, 2020 (28 pages).
"Response to Office Action," for Canadian Patent Application No. 2,912,690 filed Aug. 13, 2020 (39 pages).
"Response to Office Action," for Canadian Patent Application No. 2,912,690 filed Jan. 8, 2021 (21 pages).
"Response to Office Action," for Canadian Patent Application No. 2,912,690 filed Mar. 29, 2021 (16 pages).
"Response to Office Action," for Israeli Patent Application No. 242545 filed Jun. 7, 2020 (15 pages).
Salamone, Joseph "Hydrophilic Polymers (for Friction Reduction)," Polymeric Materials Encyclopedia, vol. 12 (1996) p. 3107.
Santoyo, Antonio B. et al., "Biosynthesis of Polyglycerol Polyricinoleate (PGPR) with Rhizopus Arrhizus Lipase," Journal of Biotechnology 131S (2007) S74-S97 2007, S82.
Scheller, Bruno et al., "Paclitaxel Balloon Coating, a Novel Method for Prevention and Therapy of Restenosis," Circulation, Journal of the American Heart Association; 2004 (110);810-814. Online version of article: http://circ.ahajournals.org/cgi/content/full/11/7/810, downloaded Jan. 12, 2011 2004, 6 pages.
"Second Office Action," for China Patent Application No. 2012800328049, mailed Jan. 26, 2016 (9 pages), with translation.
"Second Office Action," for Chinese Patent Application No. 201510411761.0 mailed Dec. 22, 2017 (11 pages) with English translation.
"Second Office Action," for Chinese Patent Application No. 2016800187265 mailed Jun. 10, 2020 (10 pages) with English Translation.
Solvay Chemicals, "Polyglycerols for Ester Production," PGLC-05-002 Revised 8-2008 CGR4004, From www.solvaychemicals.us Aug. 2008, 1-7.
Steigerwald, Kristin et al., "Vascular Healing in Drug-Eluting Stents: Differential Drug-Associated Response of Limus-Eluting Stents in a Preclinical Model of Stent Implantation," EuroIntervention, 2012. 8(6): p. 752-9 (8 pages).
Takatori, Toshihito "Design of Controlled-Release Morphine Suppositories Containing Polyglycerol Ester of Fatty Acid," Biological Pharmacy Bulletin 28(8) 1480-1484 (2005), vol. 28, No. 8 Aug. 2005, 1480-1484.

(56) References Cited

OTHER PUBLICATIONS

"Third Office Action," for Chinese Patent Application No. 2012800328049, mailed Aug. 11, 2016 (12 pages) with English translation.
"Third Office Action," for Chinese Patent Application No. 201510411761.0 mailed Jul. 25, 2018 (14 pages) with English translation.
"Third Office Action," for Chinese Patent Application No. 2016800187265 mailed Feb. 1, 2021 (11 pages) with English Translation.
"Written Submissions in Respect of Hearing on Nov. 14, 2019," for Indian Patent Application No. 3723/KOLNP/2013 filed Nov. 23, 2019 (19 pages).
Yamagata, Yutaka et al., "Novel Sustained Release Dosage Forms of Proteins Using Polyglycerol Esters of Fatty Acids," Journal of Controlled Release vol. 63, Issue 3 Feb. 3, 2000, 319-329.

* cited by examiner

ACTIVE AGENT DEPOTS FORMED IN SITU

This application claims the benefit of U.S. Provisional Application No. 62/908,236, filed Sep. 30, 2019, the content of which is herein incorporated by reference in its entirety.

FIELD

Embodiments herein relate to active agent depots formed in situ and related methods.

BACKGROUND

The human vascular system is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites (restenosis—such as that stemming from rapidly dividing smooth muscle cells). In addition, blockages can also occur in the context of peripheral arteries.

Blockages may be treated using atherectomy devices, which mechanically remove the plaque; hot or cold lasers, which vaporize the plaque; stents, which guard against mechanical recoil and hold the artery open; and other devices and procedures designed to increase blood flow through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site, and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery, preventing mechanical recoil. In rotoblation procedures, also called percutaneous transluminal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to position the blades, score the plaque and compress the fatty matter into the artery wall. During one or more of these procedures, it may be desirable to deliver a therapeutic agent or drug to the area where the treatment is occurring to prevent restenosis, repair vessel dissections or small aneurysms or provide other desired therapy.

Additionally, it may be desirable to transfer therapeutic agents to other locations in a mammal, such as the skin, neurovasculature, nasal, oral, the lungs, the mucosa, sinus, the GI tract or the renal peripheral vasculature.

SUMMARY

Embodiments herein relate to active agent depots formed in situ and related methods. In various embodiments, a method of forming an active agent depot in situ is included. The method can include contacting a composition with a vessel wall, wherein the composition includes an active agent and a fibrin promoting vessel wall transfer agent. The method also includes transferring the composition from a device surface to the vessel wall surface. The method also includes forming a fibrin matrix around the composition.

In various embodiments, a medical device is included. The medical device can include a substrate, a hydrophilic polymer layer disposed over the substrate, and an active agent layer disposed over the hydrophilic polymer layer. The active agent layer can include an active agent and a fibrin promoting vessel wall transfer agent.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
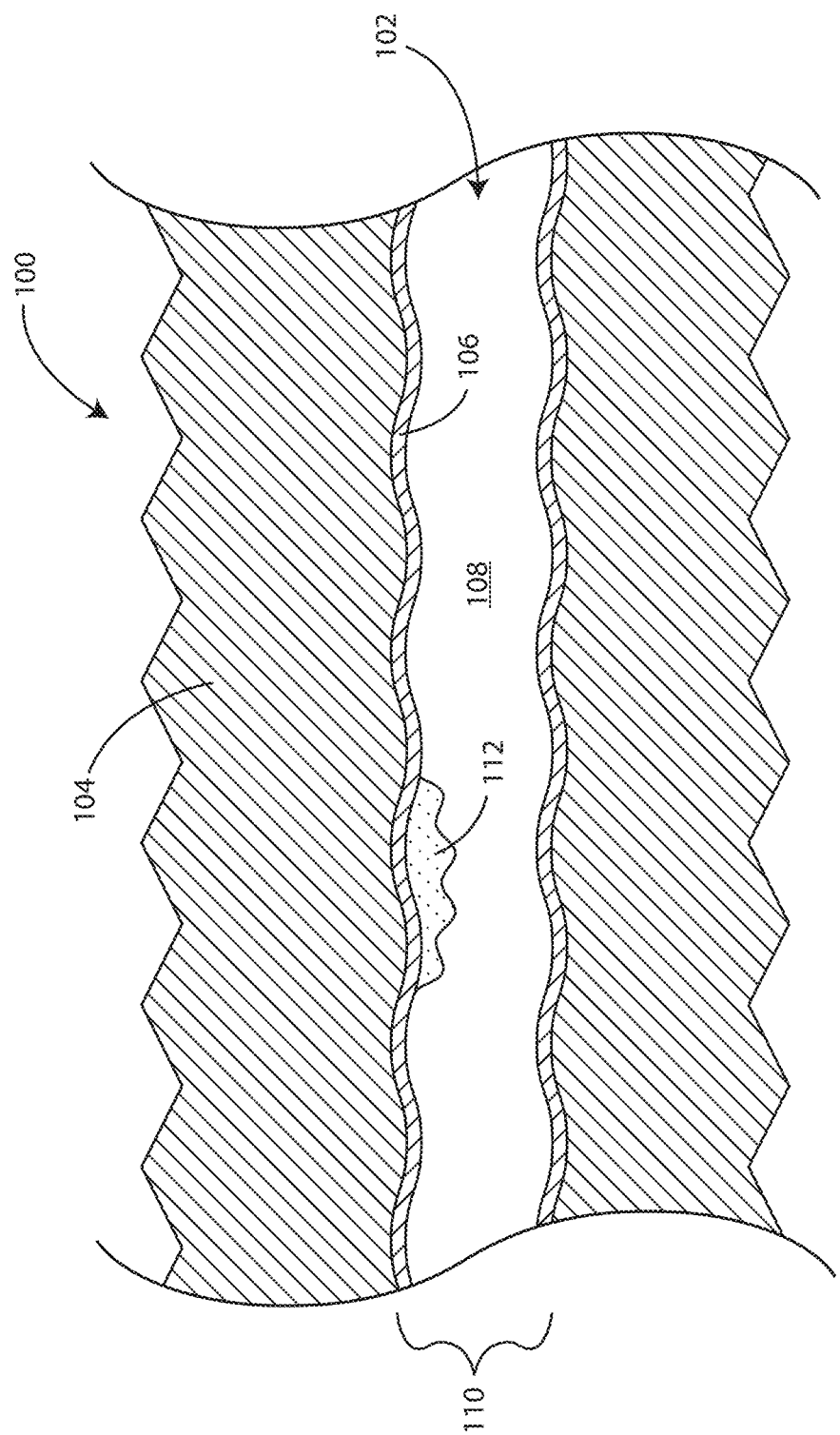
FIG. 1 is a schematic sectional view of a tissue portion to be treated in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As described above, in association with procedures such as percutaneous transluminal coronary angioplasty (PTCA), percutaneous transluminal angioplasty (PTA), and the like, it can be desirable to deliver a therapeutic agent or drug to the area where the treatment is occurring to prevent restenosis, repair vessel dissections or small aneurysms or provide other desired therapy. One approach for accomplishing this is to deliver a therapeutic agent (or active agent) to the desired tissue site using a drug delivery device such as a drug eluting balloon catheter or a drug-containing balloon catheter. It can be desirable to have the drug be present near the treated lesion over a period of time in the form of a slow release depot.

A fibrin promoting vessel wall transfer agent causes a composition including an active agent to stick to a vessel wall and attracts fibrin deposition or otherwise promotes the formation of a fibrin matrix, which in some cases can encapsulate the composition. The active agent causes the fibrin matrix to persist as fibrin. The active agent prevents or delays the fibrin matrix from being remodeled into a proteoglycan or other extracellular encapsulating matrix. As one example of an active agent, rapamycin (sirolimus) aides in the persistent presence of the fibrin matrix as it prevents remodeling of the deposited fibrin into collagen. This matrix or sheath beneficially serves to keep the delivered drug localized and limits abrasion by the bloodstream.

In various embodiments, a method of forming an active agent depot in situ is included. The method can include contacting a composition with a vessel wall, wherein the composition includes an active agent and a fibrin promoting vessel wall transfer agent. The method also includes transferring the composition from a device surface to the vessel wall surface. The method also includes forming a fibrin matrix around the composition.

In various embodiments, a medical device is included. The medical device can include a substrate, a hydrophilic polymer layer disposed over the substrate, and an active agent layer disposed over the hydrophilic polymer layer. The active agent layer can include an active agent and a fibrin promoting vessel wall transfer agent.

It has been found that ratio of amounts of the active agent to the fibrin promoting vessel wall transfer agent is significant. If too much of the fibrin promoting vessel wall transfer agent is used, then the resulting fibrin formation could become a clot itself. If too little of the fibrin promoting vessel wall transfer agent is use, then insufficient fibrin formation will result. In some embodiments, a ratio (weight: weight) of active agent to fibrin promoting vessel wall transfer agent is at least about 5:1, 7.5:1, 10:1, 12.5:1, 15:1, 17.5:1, 20:1, 22.5:1, 25:1, 27.5:1, or 30:1 or higher with respect to the amount of active agent, or a ratio falling within a range between any of the foregoing ratios.

Referring now to FIG. 1, a schematic sectional view of a tissue portion 100 to be treated is shown in accordance with various embodiments herein. The tissue portion 100 includes a vessel 102 and a tissue 104. The vessel 102 includes a vessel wall 106. The vessel 102 also includes a vessel lumen 108. The vessel 102 also includes a lesion 112.

The vessel lumen 108 has an inner diameter 110, which can be a nominal inner diameter measured at a site other than at the lesion 112. In some embodiments, the inner diameter 110 can be greater than or equal to 2 mm, 4 mm, 6 mm, 8 mm, 10 mm, 12 mm, 14 mm, 16 mm, 18 mm, 20 mm, or 22 mm, or can be an amount falling within a range between any of the foregoing.

Figure 2:
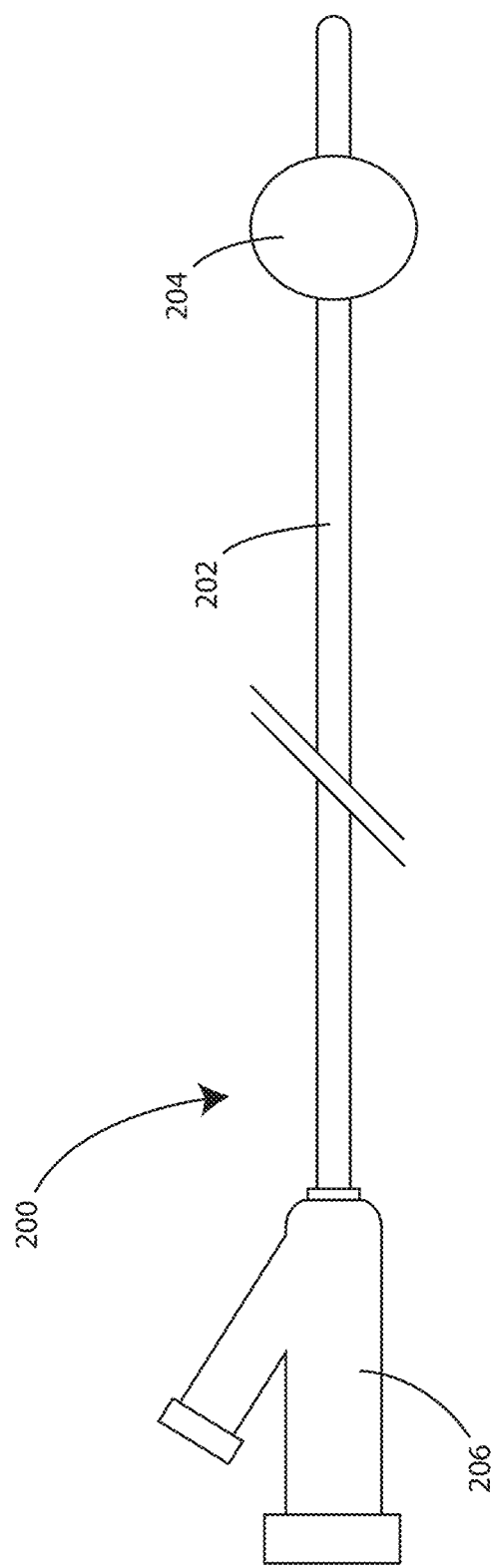
FIG. 2 is a schematic view of a medical device in accordance with various embodiments herein.

Referring now to FIG. 2, a schematic view of a medical device 200 is shown in accordance with various embodiments herein. In various embodiments, the medical device 200 can, specifically, be a balloon catheter. In this example, the medical device 200 includes a proximal manifold 206. The medical device 200 also includes a shaft 202. The medical device 200 also includes a balloon 204.

Figure 3:
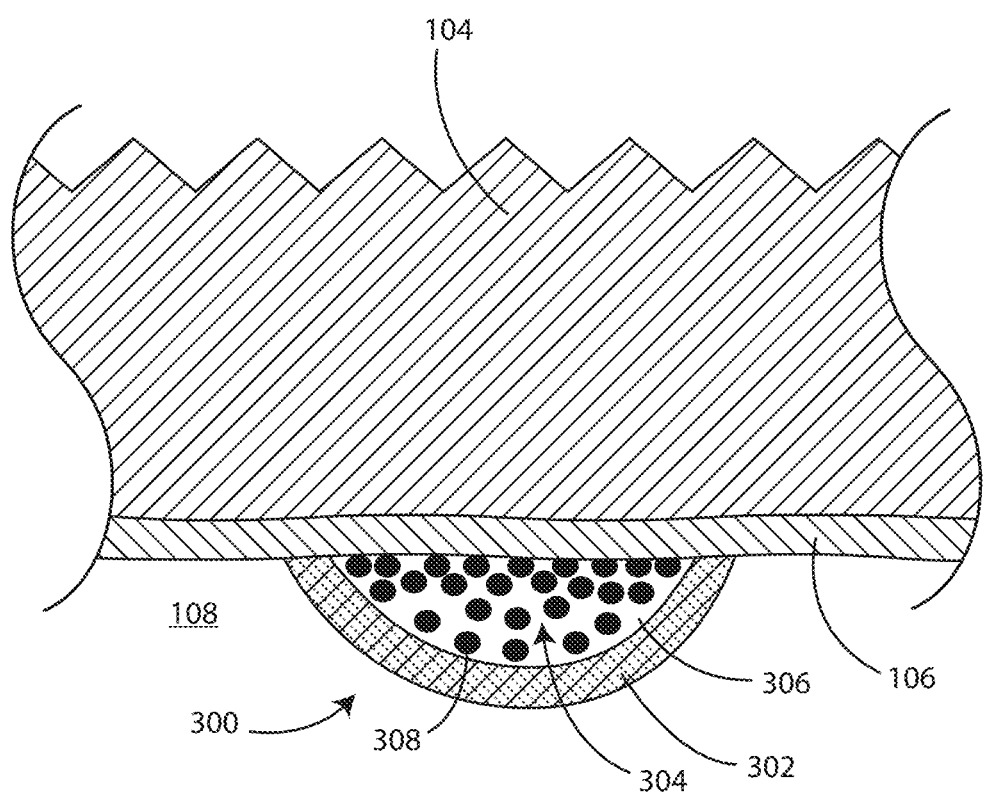
FIG. 3 is a schematic sectional view of an active agent depot formed in situ in accordance with various embodiments herein.

Referring now to FIG. 3, a schematic sectional view of an active agent depot 300 formed in situ is shown in accordance with various embodiments herein. This view shows a tissue 104, a vessel wall 106, and a vessel lumen 108.

The in situ formed active agent depot 300 includes a fibrin matrix 302. The in situ formed active agent depot 300 also includes a composition 304. The composition 304 can include many different components. However, in this example, the composition 304 includes a fibrin promoting vessel wall transfer agent 306 and an active agent 308 and fibrin or other extracellular matrix, cells etc. In various embodiments, the composition 304 can include a mixture of active agents 308.

In various embodiments, the fibrin matrix 302 can include autologous fibrin. In various embodiments, the fibrin matrix 302 can include exogenous fibrin. In some embodiments, the fibrin matrix 302 can include both autologous fibrin and exogenous fibrin.

Figure 4:
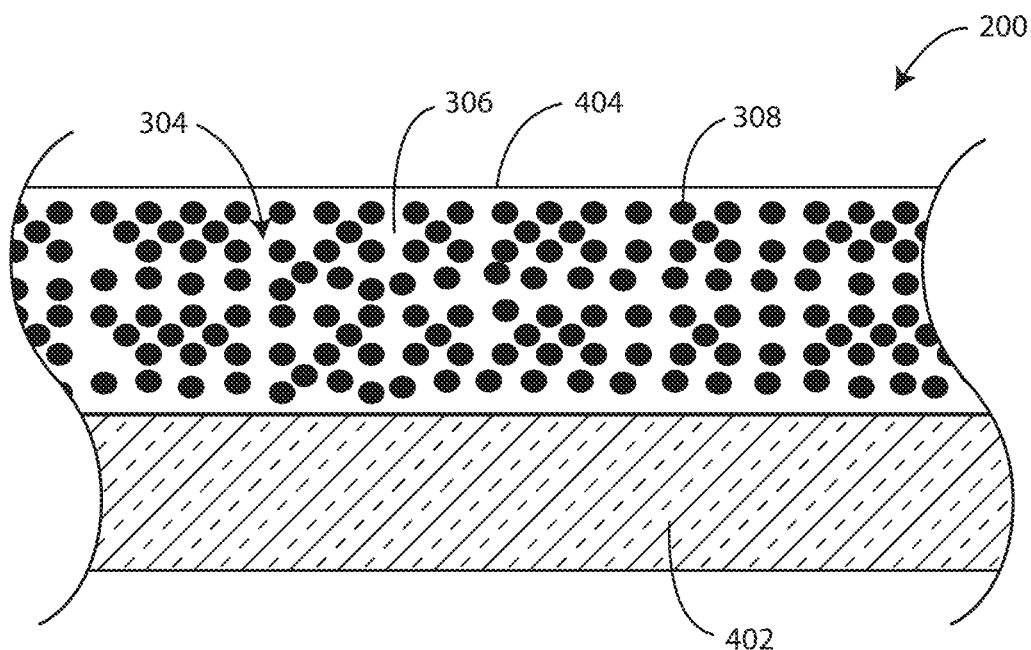
FIG. 4 is a schematic sectional view of a medical device surface in accordance with various embodiments herein.

Referring now to FIG. 4, a schematic sectional view of a medical device 200 surface is shown in accordance with various embodiments herein. The medical device 200 includes a substrate 402. The medical device 200 includes an active agent layer 404. In some embodiments, the active agent layer 404 can be disposed over a hydrophilic polymer layer (described further below). However, in some embodiments, such as shown herein the active agent layer 404 can be directly on the substrate 402. The active agent layer 404 can include various components such as a fibrin promoting vessel wall transfer agent 306 and an active agent 308 or other components as described in greater detail below.

Figure 5:
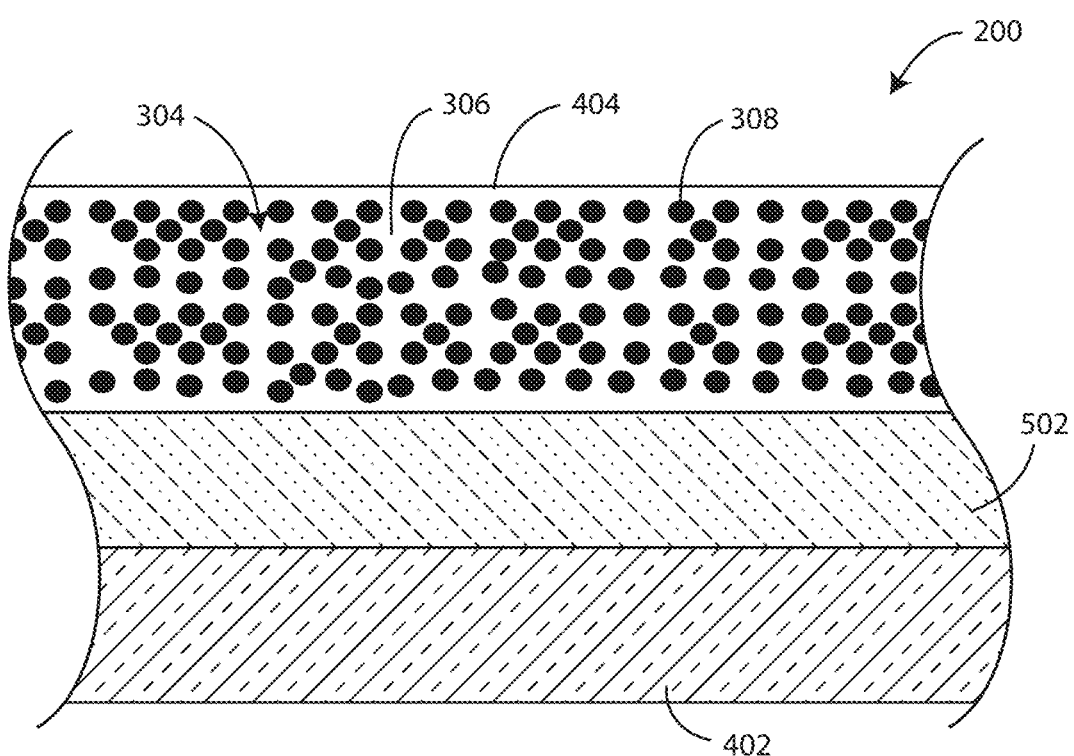
FIG. 5 is a schematic sectional view of a medical device surface in accordance with various embodiments herein.

Referring now to FIG. 5, a schematic sectional view of a medical device 200 surface is shown in accordance with various embodiments herein. The medical device 200 includes a substrate 402. The medical device 200 includes a hydrophilic polymer layer 502. In various embodiments, the hydrophilic polymer layer 502 can be disposed over the substrate 402. In some embodiments, the hydrophilic polymer layer 502 can be disposed directly on the substrate 402. In some embodiments, the hydrophilic polymer layer 502 can be disposed over the substrate 402.

The medical device 200 also includes an active agent layer 404. The active agent layer 404 can include various components such as a fibrin promoting vessel wall transfer agent 306 and an active agent 308 or other components as described in greater detail below.

Figure 6:
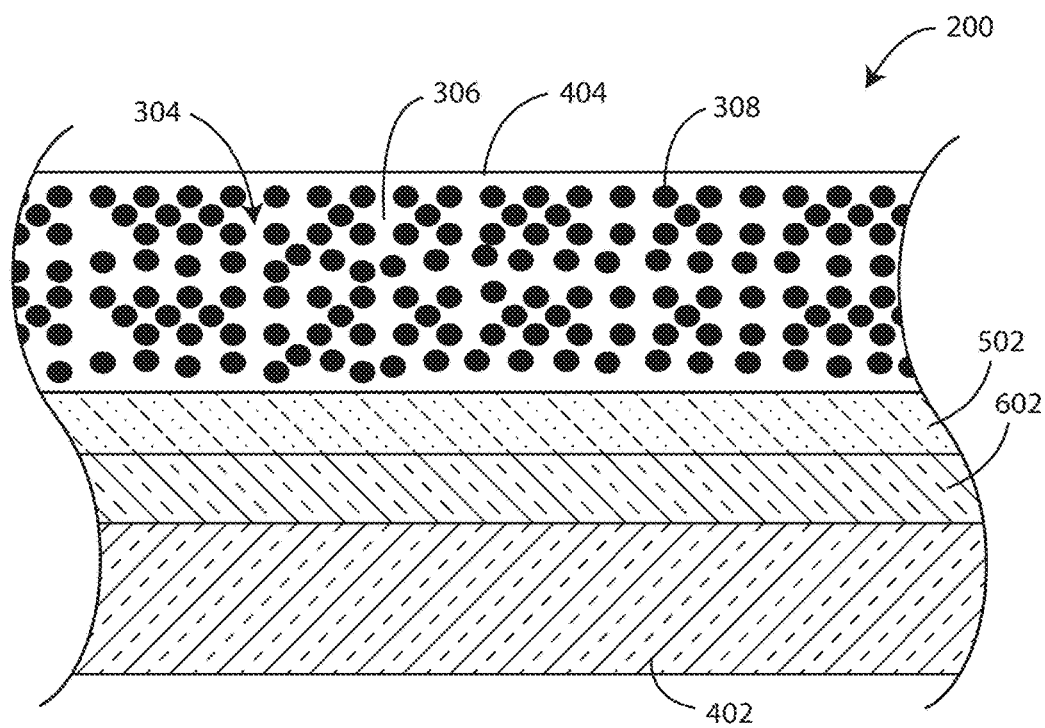
FIG. 6 is a schematic sectional view of a medical device surface in accordance with various embodiments herein.

Referring now to FIG. 6, a schematic sectional view of a medical device 200 surface is shown in accordance with various embodiments herein. The medical device 200 includes a substrate 402. The medical device 200 includes a hydrophilic polymer layer 502. In some embodiments, the medical device 200 also includes an additional polymer layer 602 (which could be an additional hydrophilic polymer layer or another type of polymer layer). The medical device 200 includes an active agent layer 404. The active agent layer 404 can include various components such as a fibrin promoting vessel wall transfer agent 306 and an active agent 308 or other components as described in greater detail below.

Figure 7:
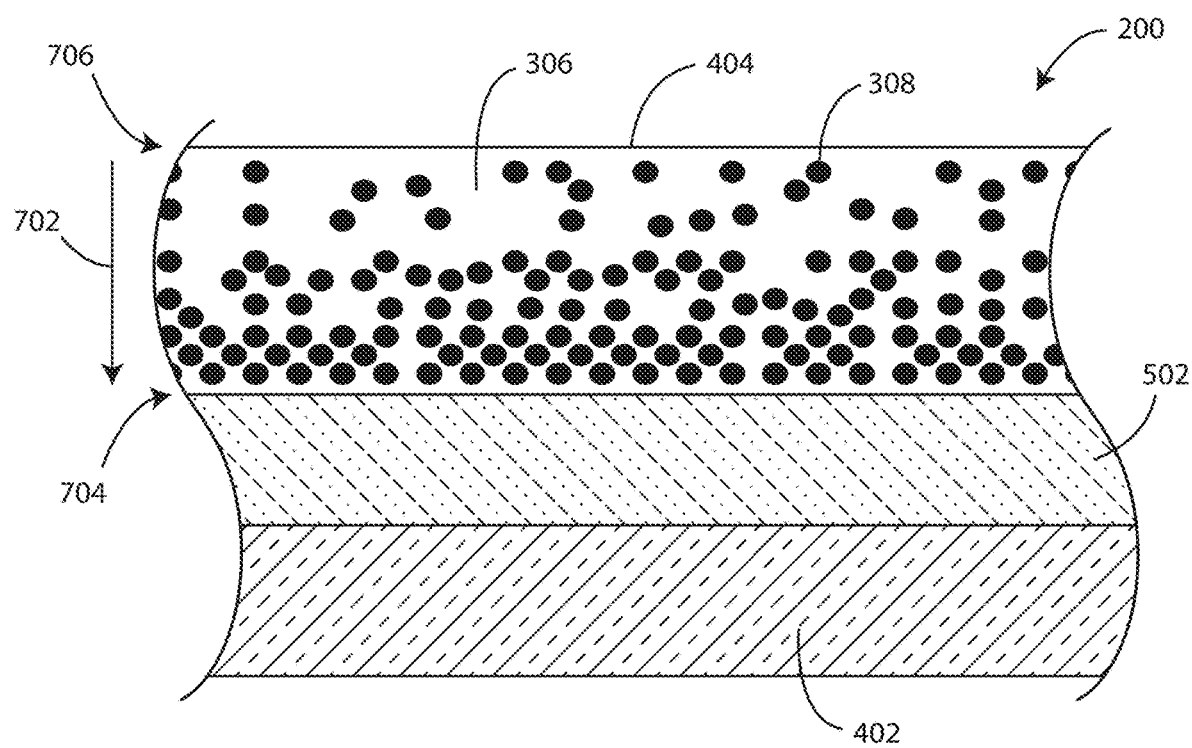
FIG. 7 is a schematic sectional view of a medical device surface in accordance with various embodiments herein.

Referring now to FIG. 7, a schematic sectional view of a medical device 200 surface is shown in accordance with various embodiments herein. The medical device 200 includes a substrate 402. The medical device 200 also includes a hydrophilic polymer layer 502. The medical device includes an active agent layer 404. The active agent layer 404 can include a composition 304 with various components such as a fibrin promoting vessel wall transfer agent 306 and an active agent 308 or other components as described in greater detail below.

The active agent layer 404 also includes an inner surface 704. The active agent layer 404 also includes an outer surface 706. The active agent layer 404 also includes a concentration gradient 702 of active agent 308 within the composition 304. In various embodiments, the concentration gradient 702 is a substantially continuous gradient. In other embodiments, the concentration gradient 702 is a non-continuous gradient.

In various embodiments, the concentration gradient 702 is between the inner surface 704 and the outer surface 706. In various embodiments, the composition 304 as disposed on the device surface has a concentration gradient 702 of the active agent 308 to the fibrin promoting vessel wall transfer agent 306 such that the concentration of the active agent 308 is higher on an inner surface 706 of the composition 304. In various embodiments, the active agent layer 404 can include an inner surface 704, and an outer surface 706, wherein the distribution of the active agent 308 within the active agent layer 404 forms a concentration gradient 702 between the inner surface 704 and the outer surface 706, with a higher concentration at the inner surface 706. However, as shown with regard to FIG. 12 below, such gradients can also be inverted.

Figure 8:
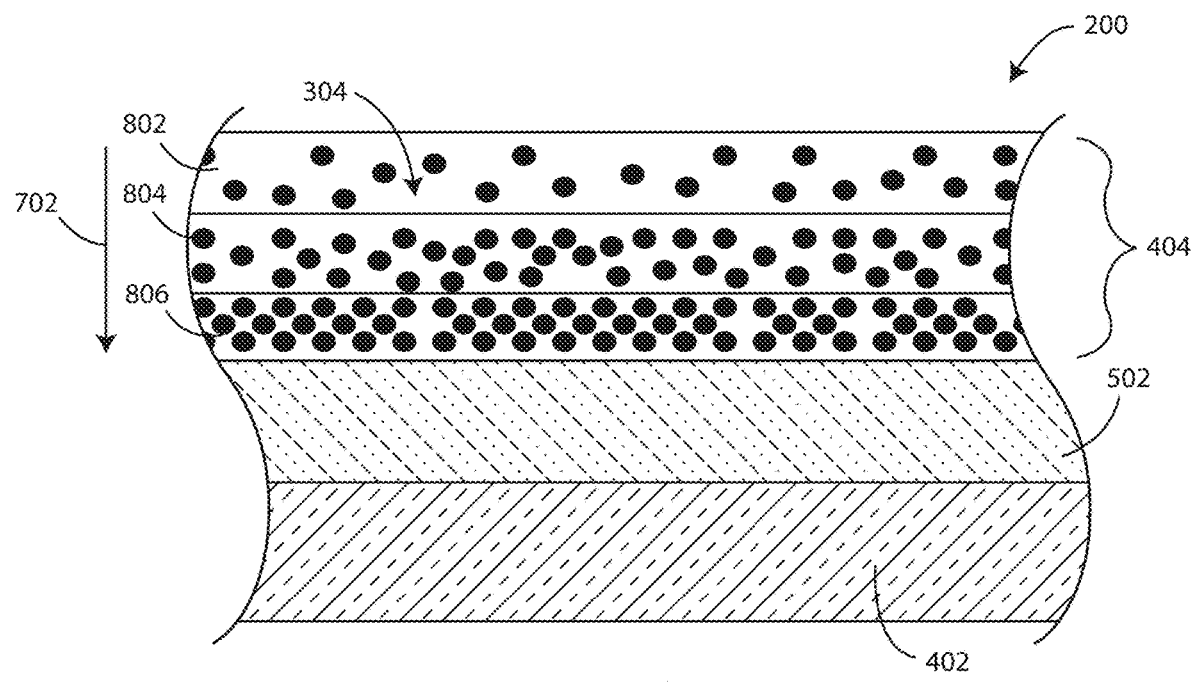
FIG. 8 is a schematic sectional view of a medical device surface in accordance with various embodiments herein.

Referring now to FIG. 8, a schematic sectional view of a medical device 200 surface is shown in accordance with various embodiments herein. The medical device 200 (not shown in this view) includes a substrate 402. The medical device 200 (not shown in this view) includes a hydrophilic polymer layer 502. The medical device 200 includes an active agent layer 404.

As described above, in some embodiments the gradient 702 may not be continuous. For example, the gradient may include one or more step change in concentration as opposed to a smooth transition in concentration. One way to achieve this is to apply different layers with different concentrations. In various embodiments, the composition 304 as disposed on the device surface comprise multiple layers with different concentrations of the active agent 308 in different layers.

Thus, in various embodiments, the active agent layer 404 can include multiple layers with different concentrations of the active agent 308 or fibrin promoting vessel wall transfer agent 306 in different layers. For example, in the embodiment illustrated in FIG. 8, the active agent layer 404 includes a first gradient layer 802. The active agent layer 404 also includes a second gradient layer 804. The active agent layer 404 also includes a third gradient layer 806.

In some embodiments, gradients can exist in regard to more than just concentration. For example, a gradient can exist with respect to particle size of active agents or other components of active agent layers herein. However, as shown with regard to FIG. 9, such gradients can also be inverted, the concentrations of an active agent as well as the particle size of the active agent can be different between the different layers or gradient layers.

Figure 9:
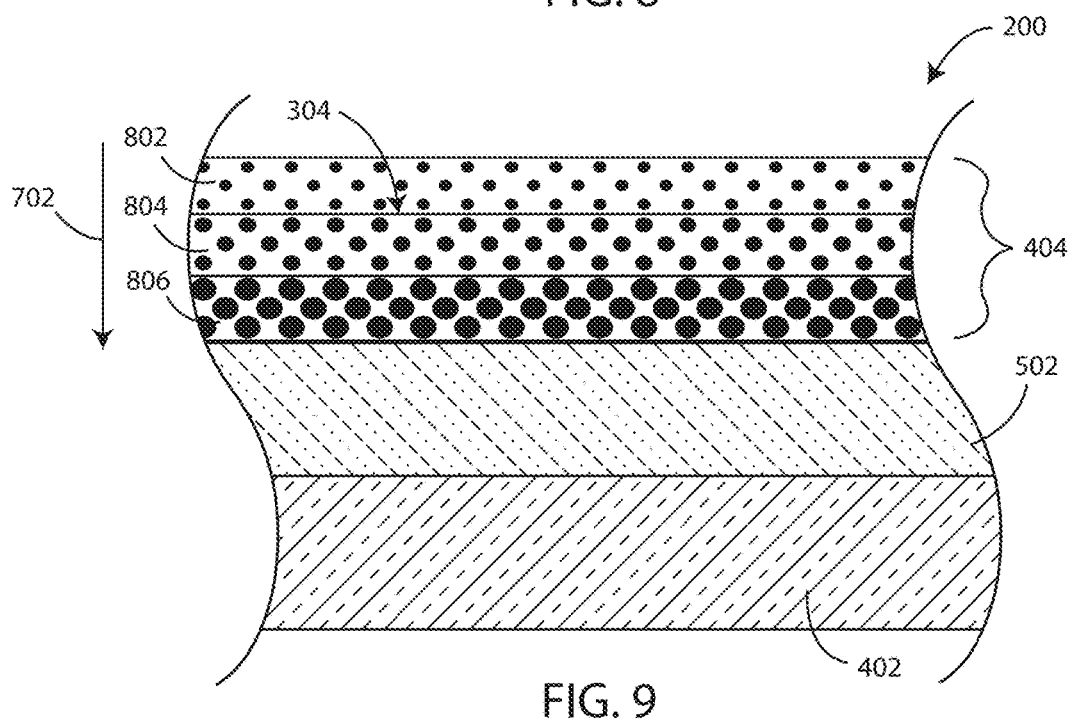
FIG. 9 is a schematic sectional view of a medical device surface in accordance with various embodiments herein.

Referring now to FIG. 9, a schematic sectional view of a medical device 200 surface is shown in accordance with various embodiments herein. The medical device 200 includes a substrate 402. A medical device (not shown in this view) includes a hydrophilic polymer layer 502. A medical device (not shown in this view) includes an active agent layer 404. The active agent layer 404 can include components of the composition 304. The active agent layer 404 includes a first gradient layer 802. The active agent layer 404 also includes a second gradient layer 804. The active agent layer 404 also includes a third gradient layer 806. In this embodiment, the concentrations of an active agent as well as the particle size of the active agent are different between the different gradient layers.

Figure 10:
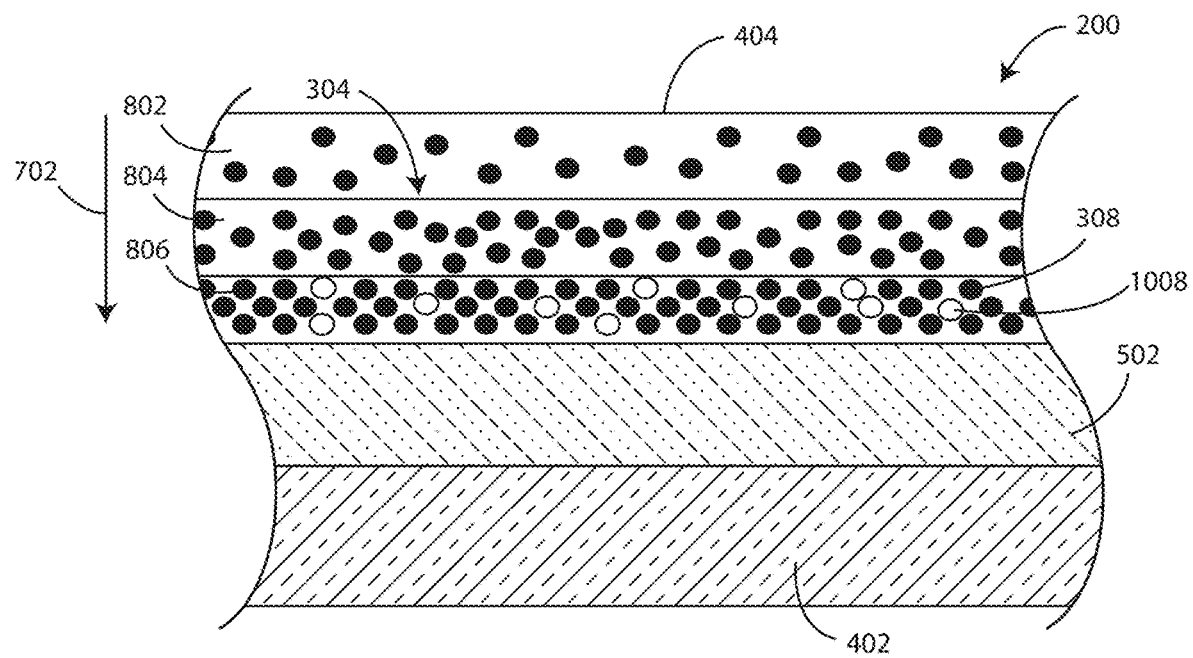
FIG. 10 is a schematic sectional view of a medical device surface in accordance with various embodiments herein.

Referring now to FIG. 10, a schematic sectional view of a medical device 200 surface is shown in accordance with various embodiments herein. The medical device 200 includes a substrate 402, a hydrophilic polymer layer 502, and an active agent layer 404.

The active agent layer 404 also includes a first gradient layer 802. The active agent layer 404 also includes a second gradient layer 804. The active agent layer 404 also includes a third gradient layer 806.

The active agent layer 404 includes a first active agent 308. The active agent layer 404 also includes a second active agent 1008. In this embodiment, the first active agent 308 is within all of the first gradient layer 802, the second gradient layer 804, and the third gradient layer 806. However, the second active agent 1008 is only within the first gradient layer 802.

In various embodiments, the active agent 308 can include a mixture of sirolimus and a second active agent 1008. In various embodiments, the active agent layer 404 can further include extracellular matrix.

In various embodiments, the active agent layer 404 can further include blood glycoprotein. In various embodiments, the active agent layer 404 can further include Von Willebrand factor. In various embodiments, the active agent layer 404 can further include at least one of fibrin or fibrinogen. In various embodiments, the active agent layer 404 can further include at least one clotting factor including at least one of clotting factor I to XIII.

Figure 11:
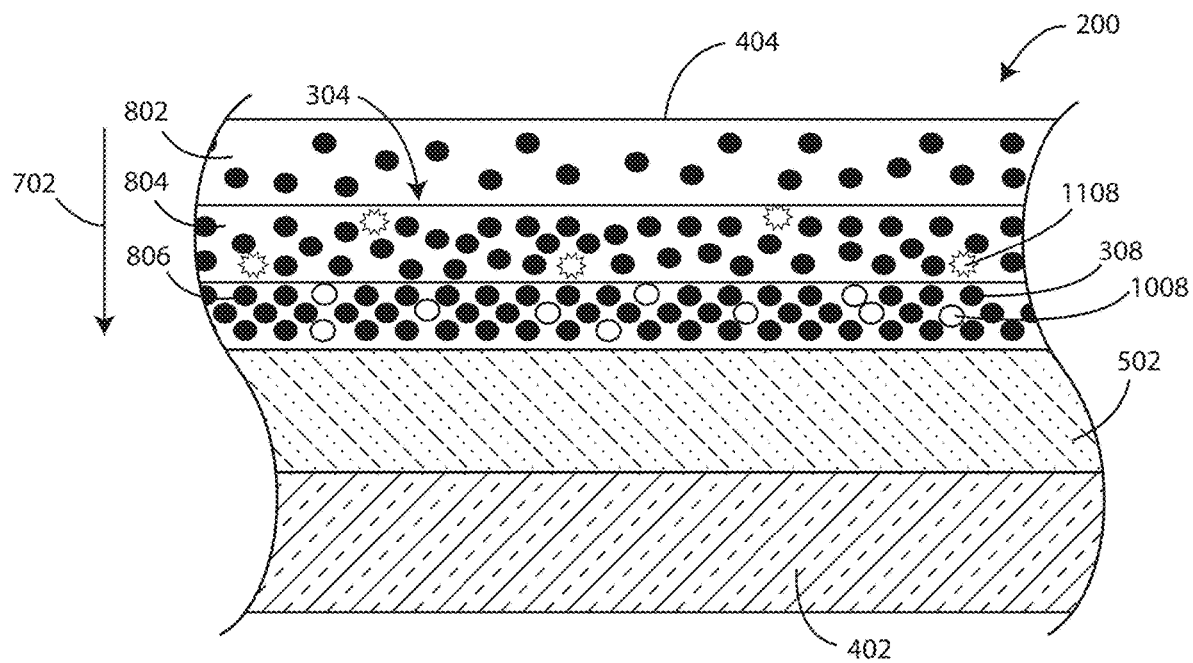
FIG. 11 is a schematic sectional view of a medical device surface in accordance with various embodiments herein.

Referring now to FIG. 11, a schematic sectional view of a medical device 200 surface is shown in accordance with various embodiments herein. The medical device 200 includes a substrate 402, a hydrophilic polymer layer 502, and an active agent layer 404.

The active agent layer 404 also includes a first gradient layer 802. The active agent layer 404 also includes a second gradient layer 804. The active agent layer 404 also includes a third gradient layer 806.

The active agent layer 404 includes a first active agent 308. The active agent layer 404 also includes a second active agent 1008. The active agent layer 404 also includes a third active agent 1108.

Figure 12:
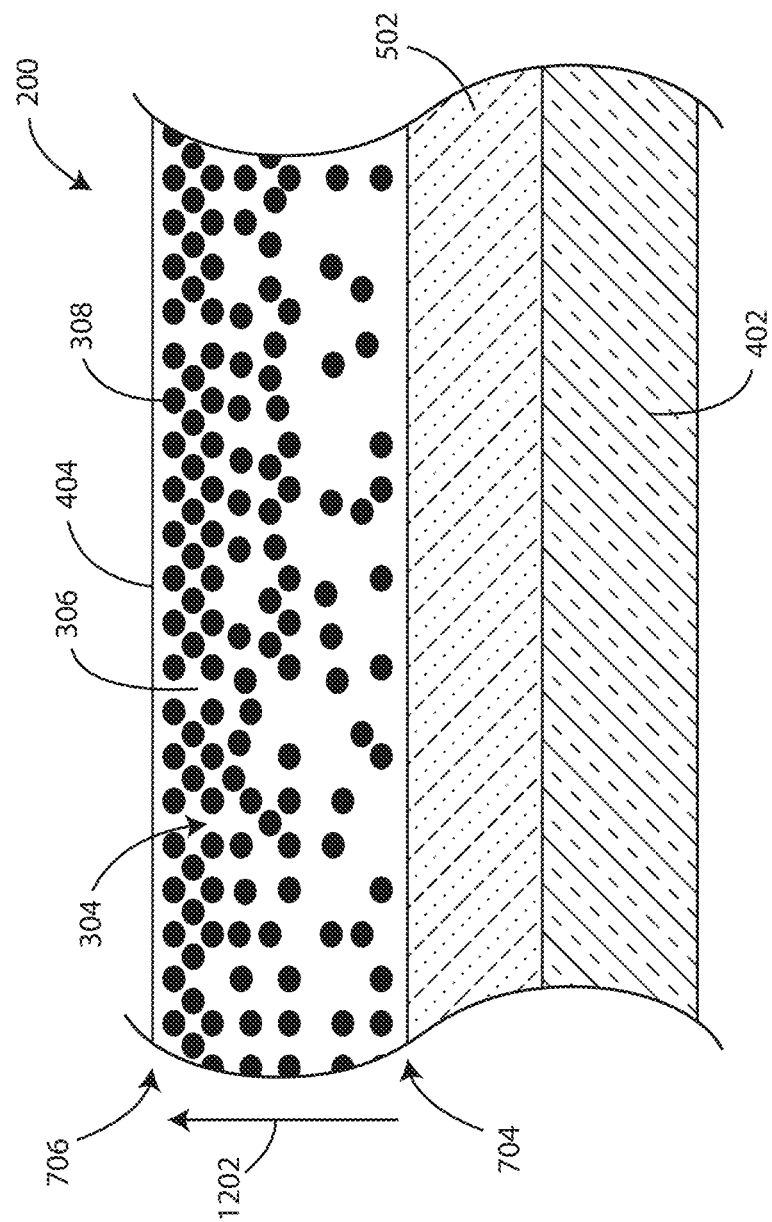
FIG. 12 is a schematic sectional view of a medical device surface in accordance with various embodiments herein.

It will be appreciated that gradients of various embodiments herein can go both ways with a higher concentration of a given component being either at the outside or the inside of an active agent layer. Referring now to FIG. 12, a schematic sectional view of a medical device 200 surface is shown in accordance with various embodiments herein. The embodiment of FIG. 12 is generally similar to FIG. 7. However, FIG. 12 illustrates a gradient 1202 that is the opposite direction as that of FIG. 7.

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of forming an active agent depot in situ is included. The method can include contacting a composition with a vessel wall, wherein the composition comprises an active agent and a fibrin promoting vessel wall transfer agent. The method can further include transferring the composition from a device surface to the vessel wall surface and forming a fibrin matrix around the composition.

In an embodiment of the method, the composition as disposed on the device surface has a concentration gradient of the active agent to the fibrin promoting vessel wall transfer agent such that the concentration of the active agent is higher on an inner surface of the composition.

In an embodiment of the method, the composition as disposed on the device surface has a concentration gradient of the active agent to the fibrin promoting vessel wall transfer agent such that the concentration of the active agent is higher on an outer surface of the composition.

In an embodiment of the method, the gradient is a continuous gradient. In an embodiment of the method, the gradient is a step change gradient.

In an embodiment of the method, the composition as disposed on the device surface comprises multiple layers with different concentrations of the active agent in different layers.

In an embodiment, the composition includes an active agent. In an embodiment, the active agent can include sirolimus. In an embodiment, the active agent can include a mixture of rapamycin and a second active agent. In an embodiment, the composition further can include extracellular matrix. In an embodiment, the composition further can include a blood glycoprotein. In an embodiment, the blood glycoprotein can include Von Willebrand factor. In an embodiment, the composition further can include at least one of fibrin or fibrinogen.

In an embodiment, the composition further can include at least one clotting factor selected from the group consisting of clotting factor I to XIII In an embodiment, the fibrin matrix can include autologous fibrin. In an embodiment, the fibrin matrix can include exogenous fibrin.

In an embodiment, a method of treating a vessel wall is included. The method can include inserting a balloon catheter into a vessel having an inner diameter of at least 4 mm and contacting a composition with a vessel wall. The composition can include an active agent and a fibrin promoting vessel wall transfer agent. The method can also include transferring the composition from a device surface to the vessel wall surface and forming a fibrin matrix around the composition.

In an embodiment of the method, the composition as disposed on the device surface has a concentration gradient of the active agent to the fibrin promoting vessel wall transfer agent such that the concentration of the active agent is higher on an inner surface of the composition as disposed on the device surface. In an embodiment of the method, the composition as disposed on the device surface comprise multiple layers with different concentrations of the active agent in different layers.

In an embodiment of the method, the composition as disposed on the device surface has a concentration gradient of the active agent to the fibrin promoting vessel wall transfer agent such that the concentration of the active agent is higher on an outer surface of the composition as disposed on the device surface. In an embodiment of the method, the composition as disposed on the device surface comprise multiple layers with different concentrations of the active agent in different layers.

Hydrophilic Base Coatings

Various embodiments herein can include a base coat disposed between the substrate and the layer including the active agent and a fibrin promoting vessel wall transfer agent. In some embodiments, the base coat can include hydrophilic polymers. In some embodiments, the base coat can include hydrophobic polymers.

One class of hydrophilic polymers useful as polymeric materials for hydrophilic base coat formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

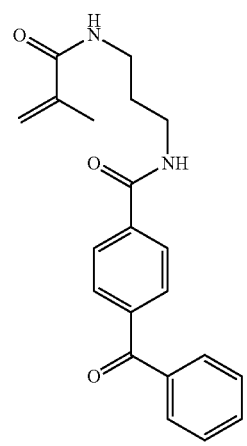

Formula I

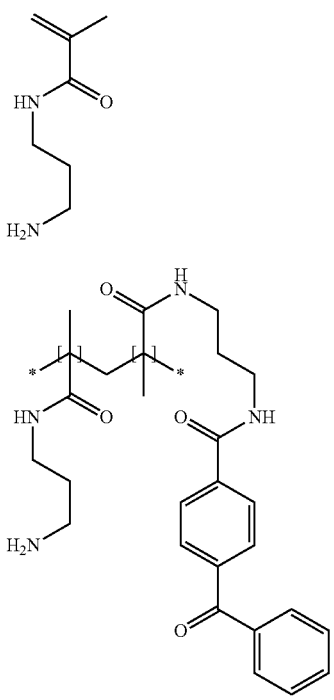

Formula II

Formula III

In some embodiments, the hydrophilic polymer can be a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacylamide), "Photo-PAA", and derivatives thereof can be used to form hydrophilic base coats in exemplary embodiments of the present disclosure. Methods for the preparation of photo-polyacrylamide are described in U.S. Pat. No. 6,007,833, the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methyl-propanesulfonate-co-N-(3-(4-benzoylbenzamido)propyl)methacrylamide)-co-methoxy poly(ethylene glycol) monomethacrylate. Other negatively charged species that can be incorporated into the hydrophilic base coat are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(meth-acryloylamino)propyl)trimethylammonium chloride. Other positively charged species that can be incorporated into the hydrophilic base coat are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat.

Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photocrosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula $Photo^1$-LG-$Photo^2$, wherein $Photo^1$ and $Photo^2$ independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula $Photo^1$-LG-$Photo^2$, wherein $Photo^1$ and $Photo^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

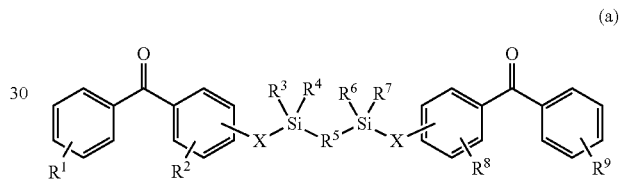

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

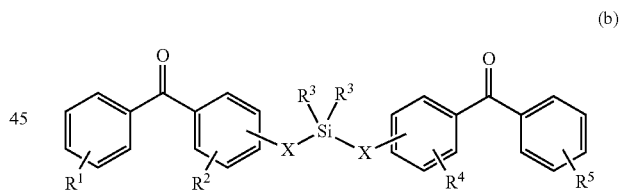

wherein R1 and R5 are any substitution; R2 and R4 can be any substitution, except OH; R3 can be alkyl, aryl, or a combination thereof; and X, independently, are O, N, Se, S, alkylene, or a combination thereof;

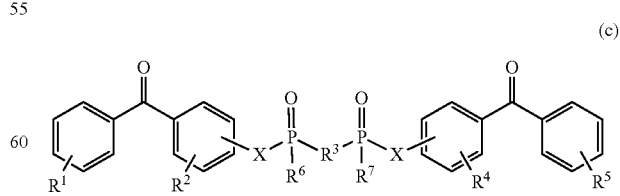

wherein R1, R2, R4 and R5 are any substitution; R3 is any substitution; R6 and R7 are alkyl, aryl, or a combination thereof; and each X can independently be O, N, Se, S, alkylene, or a combination thereof; and

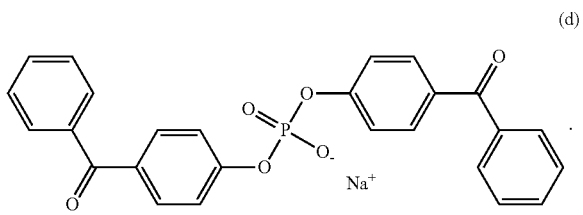

(d)

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: $X_1—Y—X_2$ where Y is a radical containing at least one acidic group, basic group, or a salt of an acidic group or basic group. $X_1$ and $X_2$ are each independently a radical containing a latent photoreactive group. The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethane-sulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition.

In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

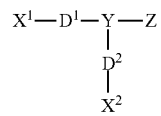

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula $XR_1R_2R_3R_4$, where X is a chemical backbone, and $R_1$, $R_2$, $R_3$, and $R_4$ are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

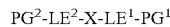

$PG^2$-$LE^2$-X-$LE^1$-$PG^1$ wherein $PG^1$ and $PG^2$ include, independently, one or more photoreactive groups, for example, an aryl ketone photoactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which is herein incorporated by reference.

In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

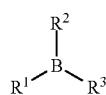

(I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—R', B—$R^2$ and B—$R^3$ can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form the hydrophilic base layer. In yet other instances the tie layer can be added to the hydrophilic base layer. The tie layer can act to increase the adhesion of the hydrophilic base layer to the substrate. In other embodiments, the tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

Substrates

The substrate can be formed from any desirable material, or combination of materials, suitable for use within the body. In some embodiments the substrate is formed from compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single elastomeric material, or a combination of materials.

Other materials for the substrate can include those formed of polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Beyond polymers, and depending on the type of device, the substrate can also be formed of other inorganic materials such as metals (including metal foils and metal alloys), glass and ceramics.

Processes to modify substrates described above can include chemical modifications to improve performance characteristics of the substrate. Specific chemical processes that can be used include ozone treatment, chemical oxidation, acid chemical etching, base chemical etching, plasma treatment and corona treatment, surface grafting, thermally activated coating processes (both covalent and non-covalent) and surface modifications including coatings containing dopamine, tannic acid, plant polyphenols and other catechols or catechol containing derivatives of hydrophilic moieties. Additionally, processes to form substrates described above can include physical modifications for example, but not limited to, sand blasting and surface texturing (for example either during or after the molding process of polymers).

In some embodiments, the modification of substrates as described herein can allow for omission of a base coating layer (such as a hydrophilic layer) as substrate surfaces that have been modified will allow for improved adhesion of a hydrophobic therapeutic agent and cationic agent compared with that of a hydrophilic layer.

Active Agents

It will be appreciated that active agents of embodiments herein can include agents having many different types of activities. In various embodiments herein, active agents can specifically include hydrophobic active agents. The terms "active agent" and "therapeutic agent" as used herein shall be coterminous unless the context dictates otherwise. Hydrophobic active agents can specifically include those having solubility in water of less than about 100 µg/mL at 25 degrees Celsius and neutral pH. In various embodiments, hydrophobic active agents can specifically include those having solubility in water of less than about 10 µg/mL at 25 degrees Celsius and neutral pH. In some embodiments, hydrophobic active agents can specifically include those having solubility in water of less than about 5 µg/ml at 25 degrees Celsius and neutral pH.

In some exemplary embodiments, active agents can include, but are not limited to, antiproliferatives such as paclitaxel and limus drugs such as sirolimus (rapamycin), rapalogs, zotarolimus, everolimus, temsirolimus, pimecrolimus, tacrolimus, and ridaforolimus; analgesics and anti-inflammatory agents such as aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; antibacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate; therapeutic peptides and proteins, and the like.

Other exemplary embodiments of active agents include, but are not limited to, active agents for treatment of hypertension (HTN), such as guanethidine.

In a particular embodiment, the hydrophobic active agents are selected from the group consisting of paclitaxel, sirolimus (rapamycin), rapalogs, and mixtures thereof.

In some exemplary embodiments, active agents used herein can include a first active agent such as an antiproliferative such as rapamycin or a rapalog and a second active agent such as a non-proliferative, such as any of the other active agents described herein.

In some embodiments, a hydrophobic active agent can be conjugated to a cationic agent. The conjugation can include a hydrophobic active agent covalently bonded to the cationic agent. In some embodiments wherein the hydrophobic agent is conjugated to the cationic agent a linking agent can be used to attach the hydrophobic agent to the cationic agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

Particle size and size distribution of a particulate preparation can be determined using any one of various techniques known in the art. In one mode of practice, laser diffraction can be used to measure particle size and distribution. In laser diffraction a laser beam passes through a dispersed particulate sample and angular variation in intensity of light scattered is measured. The angle of light scattering is greater for large particles and less for smaller particles, and the angular scattering intensity data can be collected and analyzed to generate a particle size profile.

Analysis of particulate size and distribution can be performed using laser light scattering equipment such as Malvern System 4700, (for particles from 1 nm to 3 µm) or Horiba LA-930 (e.g., for particles from 100 nm to 2 mm). The output from such analyzers can provide information on the sizes of individual particulates, and the overall amount of particulates of these sizes reflecting the distribution of particulates in terms of size. Analysis providing data on the size distribution can be provided in the form of a histogram, graphically representing the size and size distribution of all the particulates in a preparation.

Exemplary particulate hydrophobic therapeutic agents can have different morphological characteristics. In some embodiments the particulate hydrophobic therapeutic agent can be crystalline. In yet other embodiments of the present disclosure the particulate hydrophobic therapeutic agent can be amorphous. Additionally, combinations of crystalline and amorphous particulate hydrophobic therapeutic agents can be desirable in order to achieve, for example, desired solubilities of the particulate hydrophobic therapeutic agents.

In some embodiments, the particulate hydrophobic therapeutic agent can have an average diameter ("dn", number average) that is less than about 30 µm or less than about 10 µm. Also, in some embodiments, the particulate hydrophobic therapeutic agent can have an average diameter of about 100 nm or larger. For example, the microparticulates associated with the expandable elastic portion can have an average diameter in the range of about 100 nm to about 10 µm, about 150 nm to about 2 µm, about 200 nm to about 5 µm, or about 0.3 µm to about 1 µm.

Fibrin Promoting Vessel Wall Transfer Agents

In various embodiments herein, compositions including active agents and/or active agent layers herein can include other compounds. For example, such compositions can specifically include a fibrin promoting vessel wall transfer agent. The fibrin promoting vessel wall transfer agent can function to attract fibrin and/or cause or promote the formation of a fibrin matrix. The fibrin promoting vessel wall transfer agent can also function to cause or promote adherence of the composition to a vessel wall.

In various embodiments herein, the fibrin promoting vessel wall transfer agent can be a charged transfer agent. In various embodiments herein, the fibrin promoting vessel wall transfer agent can be a cationic agent. In various embodiments herein, the fibrin promoting vessel wall transfer agent can be a polycationic agent.

Cationic agents used in embodiments herein can include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic agents used in embodiments herein can include those having the general formula X-Y, wherein X is a radical including a positively charged group in aqueous solution at neutral pH and Y is a radical exhibiting hydrophobic properties. In some embodiments, the cationic agent can include a hydrophilic head and a hydrophobic tail, along with one or more positively charged groups, typically in the area of the hydrophilic head.

Cationic agents of the present disclosure can include salts of cationic agents at various pH ranges, such as, but not limited to, halide salts, sulfate salts, carbonate salts, nitrate salts, phosphate salts, acetate salts and mixtures thereof.

Cationic agents can specifically include cationic lipids and net neutral lipids that have a cationic group (neutral lipids with cationic groups). Exemplary lipids can include, but are not limited to, 3β[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE). Other cationic agents can include mono- or polyaminoalkanes such as spermine and spermidine.

Cationic agents can specifically include cationic polymers. Cationic agents can also include polycation-containing cyclodextrin (for example, but not limited to, amino cyclodextrin and derivatives thereof), amino dextran, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polyallylamine, polypropylenimine, polyamidoamine dendrimers (PAMAM; available from Sigma Aldrich), cationic polyoxazoline and poly(beta-aminoesters). Cationic agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers. Other exemplary cationic agents include positively charged gelatin (for example, base-treated gelatin), and the family of aminated cucurbit[n]urils (wherein n=5, 6, 7, 8, 10).

In other embodiments of the present disclosure, cationic agents containing a portion having a positive charge in aqueous solutions at neutral pH include the following Compounds (A-I):

Compound A

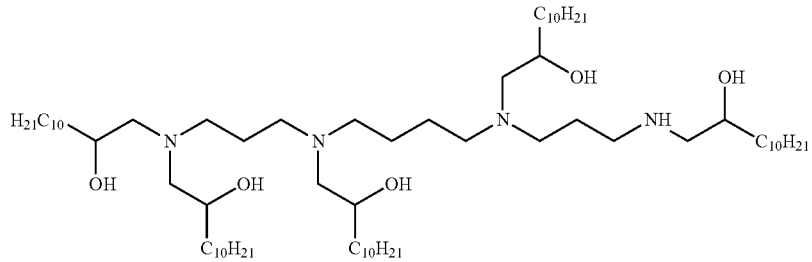

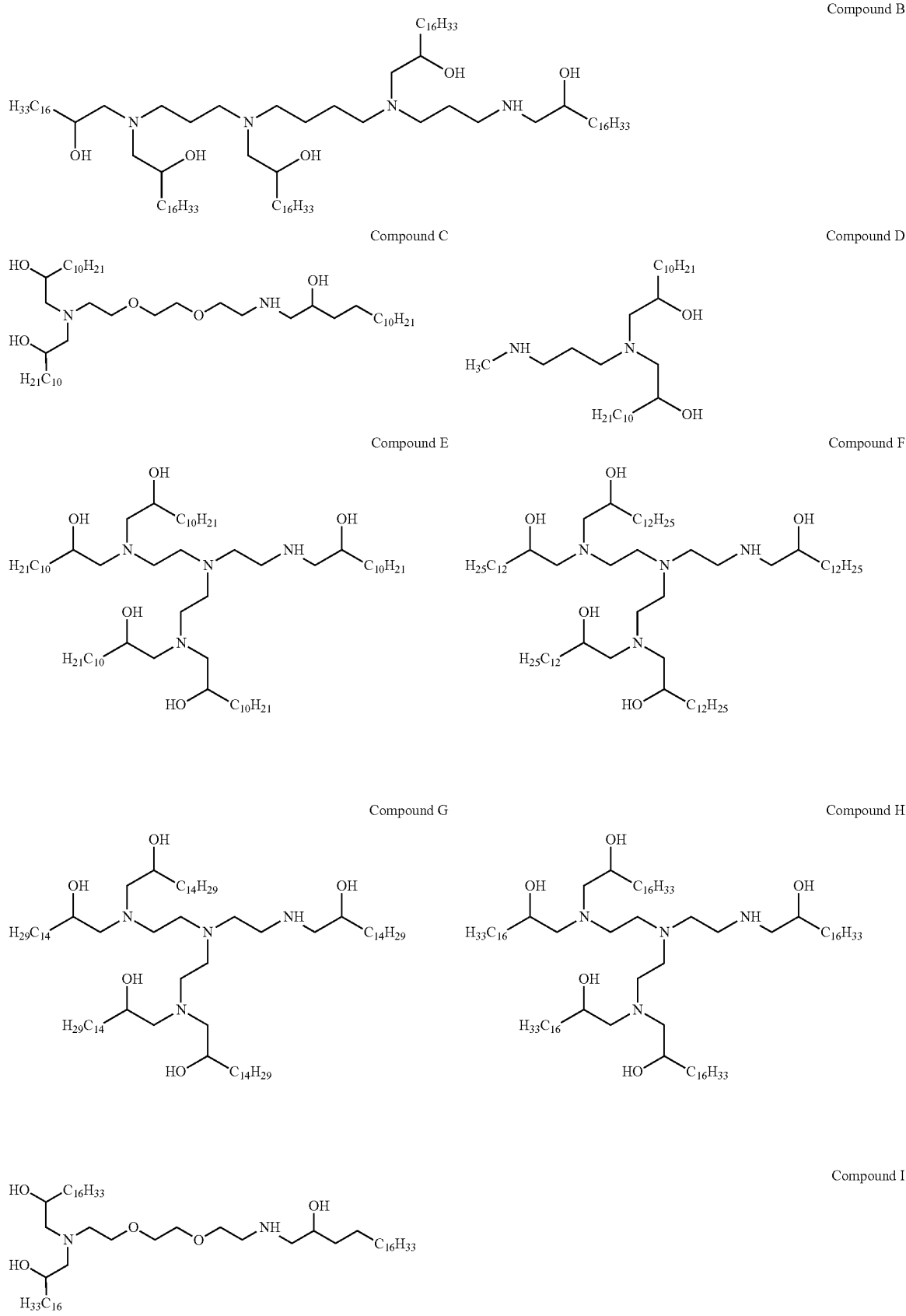

Additionally, other cationic agents include structures of the general Formula I:

Formula I

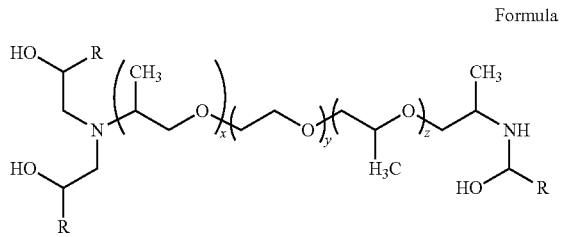

TABLE 1

Values for Variables x + z,
y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Cationic agents, such as those listed above, can generally be prepared by the reaction of an appropriate hydrophobic epoxide (e.g. oleyl epoxide) with a multifunctional amine (e.g. propylene diamine). Details of the synthesis of related cationic agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic agents can include moieties used to condense nucleic acids (for example lipids, peptides and other cationic polymers). In some instances these cationic agents can be used to form lipoplexes and polyplexes.

Exemplary embodiments of cationic agents can also include, but are not limited to, cationic agent derivatives that are photo reactive. Photo reactive groups are described below. Such cationic agent derivatives include PEI polymer derivatives of benzophenone and PAMAM polymer derivatives of benzophenone.

In some embodiments, the molecular weight of the cationic agent can be about 1.2 kDa, 2.5 kDa, 10 kDa, 25 kDa, 250 kDa or even, in some cases, 750 kDa. In yet other embodiments the molecular weight of the cationic agent can be in the range of 50-100 kDa, 70-100 kDa, 50-250 kDa, 25-100 kDa, 2.5-750 kDa or even, in some cases, 2.5-2,000 kDa. Other embodiments include molecular weights greater than 1.2 kDa, 2.5 kDa, 10 kDa, 25 kDa, 250 kDa or even, in some cases, greater than 750 kDa. Other embodiments can include cationic agents up to 2,000 kDa.

Low molecular weight cationic agent monomers or low molecular weight cationic oligomers can be combined with hydrophobic active agent to produce a reactive coating. These reactive coatings can then be coated onto a substrate and thermally polymerized or polymerized with UV-radiation. Exemplary monomers include, but are not limited to, aziridine, vinylamine, allylamine and oligomers from 80 g/mol to 1200 g/mol. Crosslinkers (e.g., 1,2-dichloroethane, epichlorohydrin, 1,6-diisocyanatohexane) could be used to crosslink oligomers.

Medical Devices

It will be appreciated that embodiments herein include, and can be used in conjunction with, various types of medical devices including, but not limited to, drug delivery devices such as drug eluting balloon catheters, drug-containing balloon catheters, stents, grafts, and the like.

Some embodiments described herein can be used in conjunction with balloon expandable flow diverters, and self-expanding flow diverters. Other embodiments can include uses in contact with angioplasty balloons (for example, but not limited to, percutaneous transluminal coronary angioplasty and percutaneous transluminal angioplasty). Yet other embodiments can include uses in conjunction with sinoplasty balloons for ENT treatments, urethral balloons and urethral stents for urological treatments and gastro-intestinal treatments (for example, devices used for colonoscopy). Hydrophobic active agent can be transferred to tissue from a balloon-like inflatable device or from a patch-like device. Other embodiments of the present disclosure can further be used in conjunction with micro-infusion catheter devices. In some embodiments, micro-infusion catheter devices can be used to target active agents to the renal sympathetic nerves to treat, for example, hypertension.

Other exemplary medical applications wherein embodiments of the present disclosure can be used further encompass treatments for bladder neck stenosis (e.g. subsequent to transurethral resection of the prostrate), laryngotrachial stenosis (e.g. in conjunction with serial endoscopic dilatation to treat subglottic stenosis, treatment of oral cancers and cold sores and bile duct stenosis (e.g. subsequent to pancreatic, hepatocellular of bile duct cancer). By way of further example, embodiments herein can be used in conjunction with drug applicators. Drug applicators can include those for use with various procedures, including surgical procedures, wherein active agents need to be applied to specific tissue locations. Examples can include, but are not limited to, drug applicators that can be used in orthopedic surgery in order to apply active agents to specific surfaces of bone, cartilage, ligaments, or other tissue through physical contact of the drug applicator with those tissues. Drug applicators can include, without limitation, hand-held drug applicators, drug patches, drug stamps, drug application disks, and the like.

In use, various embodiments included herein can enable rapid transfer of therapeutic agents to specific targeted tissues. For example, in some embodiments, a care provider can create physical contact between a portion of a drug delivery device including a therapeutic agent and the tissue being targeted and the therapeutic agent will be rapidly transferred from the drug delivery device to that tissue. As such, precise control over which tissues the therapeutic agent is provided to can be achieved.

One beneficial aspect of various embodiments described herein is that the therapeutic agent can be transferred from the drug delivery device or coating to the targeted tissue very rapidly. In some embodiments substantial transfer of the therapeutic agent from the drug delivery device or coating to the tissue occurs in 30 minutes or less. In some embodiments substantial transfer of the therapeutic agent from the drug delivery device or coating to the tissue occurs in 15 minutes or less. In some embodiments substantial transfer of the therapeutic agent from the drug delivery device or coating to the tissue occurs in 10 minutes or less. In some embodiments substantial transfer of the therapeutic agent from the drug delivery device or coating to the tissue occurs in 5 minutes or less. In some embodiments substantial transfer of the therapeutic agent from the drug delivery device or coating to the tissue occurs in 2 minutes or less. In some embodiments substantial transfer of the therapeutic agent from the drug delivery device or coating to the tissue occurs in 1 minute or less.

Aspects may be better understood with reference to the following examples. These examples are intended to be representative of specific embodiments, but are not intended as limiting the overall scope of embodiments herein.

EXAMPLES

Example 1: In Situ Formation of Active Agent Depot

A composition was prepared including microcrystalline sirolimus and polyethyleneimine as a fibrin promoting vessel wall transfer agent. The composition was coated onto a balloon of a balloon catheter that was previously coated with a hydrophilic polymer composition.

The coated balloon catheter was inserted into a vessel having a diameter of approximately 3.5 mm of a 35 kg pig. The balloon was expanded and left in place for approximately 180 seconds before being deflated. The coated balloon catheter was then withdrawn.

Approximately 30 days after the balloon catheter procedure, the vessel was harvested and sectioned for histological analysis.

Figure 13:
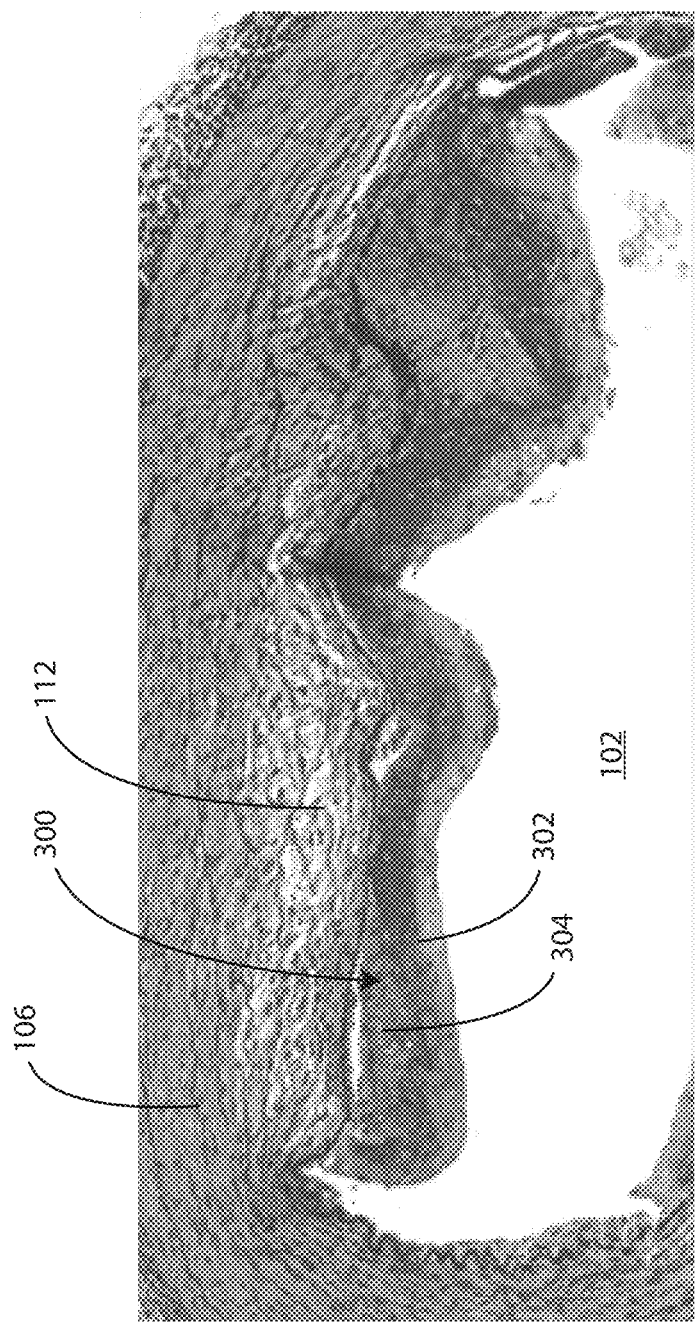
FIG. 13 is a schematic sectional view of a vessel including an in situ formed active agent depot in accordance with various embodiments herein.

The result is shown in FIG. 13, which is a sectional view of a vessel 102 including an in situ formed active agent depot 300. The vessel 102 includes a vessel wall 106 and a lesion 112. The in situ formed active agent depot 300 included a fibrin matrix 302. The in situ formed active agent depot 300 included a composition 304, which contained active agent particles therein.

Example 2: In Situ Formation of Active Agent Depot and Effects of Different Fibrin Promoting Vessel Wall Transfer Agents and Vessels Compositions were prepared including microcrystalline sirolimus and either polyethyleneimine (PEI) or polyvinylamine (PVAm) as a fibrin promoting vessel wall transfer agent. The compositions were coated onto balloons of balloon catheters (with balloon sizes of 15 mm or 40 mm) that were previously coated with a hydrophilic polymer composition. The amount of the sirolimus was varied so as to provide different dosages to the tissue, including 3 $\mu g/mm^2$, 8 $\mu g/mm^2$, and 10 $\mu g/mm^2$.

The coated balloon catheter was inserted into vessels (PTCA coronary, PTA peripheral, PTCA peripheral) of a 35 kg pig. The balloon was expanded and left in place for approximately 180 seconds before being deflated. The coated balloon catheter was then withdrawn.

Approximately 30 days after the balloon catheter procedure, the vessel was harvested and evaluated and scored for the presence of fibrin.

Figure 14:
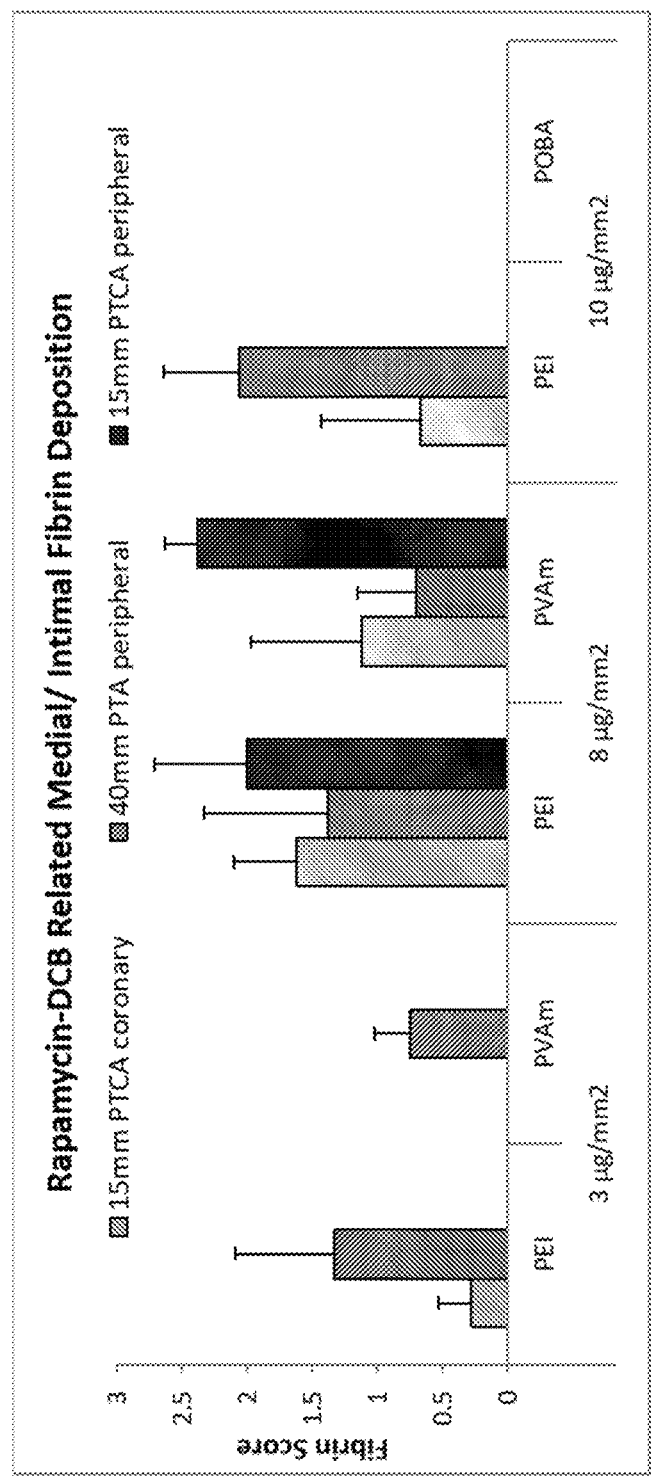
FIG. 14 is a chart showing medial/intimal fibrin deposition.

The results are shown in FIG. 14, which shows medial/intimal fibrin deposition. While not intending to be bound by theory, this example shows that PEI was more effective as a fibrin promoting vessel wall transfer agent than PVAm.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of forming an active agent releasing depot in situ comprising
  contacting a layer of a composition with a vessel wall;
  wherein the composition comprises
    a first gradient layer comprising a first active agent;
    a second gradient layer comprising the first active agent and a second active agent, wherein the first gradient layer is disposed over the second gradient layer; and
    a third gradient layer comprising the first active agent and a third active agent, wherein the second gradient layer is disposed over the third gradient layer;
    wherein the first gradient layer, the second gradient layer, and the third gradient layer all comprise a fibrin promoting vessel wall transfer agent;
    wherein the composition has an increasing concentration gradient of the first active agent from the first gradient layer to the third gradient layer;

transferring the layer of the composition from a device surface to the vessel wall surface; and forming an initial fibrin matrix around the composition.

2. The method of claim 1, wherein the fibrin promoting vessel wall transfer agent is a polyvinylamine (PVAm).

3. The method of claim 1, wherein the fibrin promoting vessel wall transfer agent is a charged transfer agent.

4. The method of claim 1, wherein the fibrin promoting vessel wall transfer agent is a cationic agent.

5. The method of claim 1, wherein the fibrin promoting vessel wall transfer agent is a polycationic agent.

6. The method of claim 1, wherein the fibrin promoting vessel wall transfer agent is polyethyleneimine.

7. The method of claim 1, the first active agent comprising sirolimus.

8. The method of claim 1, the fibrin matrix comprising autologous fibrin.

9. The method of claim 1, the fibrin matrix comprising exogenous fibrin.

10. The method of claim 1, the composition further comprising extracellular matrix.

11. The method of claim 1, the composition further comprising a blood glycoprotein.

12. The method of claim 11, the blood glycoprotein comprising Von Willebrand factor.

13. The method of claim 1, the composition further comprising at least one of fibrin or fibrinogen.

14. The method of claim 1, the composition further comprising at least one clotting factor selected from the group consisting of clotting factor I to XIII.

15. The method of claim 1, wherein the fibrin matrix is remodeled over time to proteoglycan or other extracellular matrix with or without cells.

* * * * *